United States Patent
Leighton et al.

(10) Patent No.: US 12,408,640 B2
(45) Date of Patent: *Sep. 9, 2025

(54) TRANSGENIC ANIMAL FOR PRODUCING DIVERSIFIED ANTIBODIES THAT HAVE THE SAME LIGHT CHAIN I

(71) Applicant: Crystal Bioscience Inc., Emeryville, CA (US)

(72) Inventors: Philip A. Leighton, San Francisco, CA (US); William Don Harriman, Alameda, CA (US); Robert Etches, Oakland, CA (US)

(73) Assignee: CRYSTAL BIOSCIENCE INC., Emeryville, CA (US)

( * ) Notice: Subject to any disclaimer, the term of this patent is extended or adjusted under 35 U.S.C. 154(b) by 600 days.

This patent is subject to a terminal disclaimer.

(21) Appl. No.: 17/728,874

(22) Filed: Apr. 25, 2022

(65) Prior Publication Data

US 2022/0256820 A1    Aug. 18, 2022

Related U.S. Application Data

(63) Continuation of application No. 15/734,187, filed on Dec. 1, 2020, now Pat. No. 11,337,409, which is a continuation-in-part of application No. PCT/US2019/035526, filed on Jun. 5, 2019.

(60) Provisional application No. 62/684,529, filed on Jun. 13, 2018, provisional application No. 62/682,651, filed on Jun. 8, 2018.

(51) Int. Cl.
| | |
|---|---|
| *A01K 67/0275* | (2024.01) |
| *C07K 16/00* | (2006.01) |
| *C12N 5/0781* | (2010.01) |
| *C12N 15/02* | (2006.01) |
| *C12N 15/85* | (2006.01) |

(52) U.S. Cl.
CPC .......... *A01K 67/0275* (2013.01); *C07K 16/00* (2013.01); *C12N 5/0635* (2013.01); *C12N 15/02* (2013.01); *C12N 15/8509* (2013.01); *A01K 2217/05* (2013.01); *A01K 2217/07* (2013.01); *A01K 2227/30* (2013.01); *A01K 2267/01* (2013.01); *C07K 2317/14* (2013.01); *C07K 2317/56* (2013.01)

(58) Field of Classification Search
CPC ........... A01K 67/0275; A01K 2217/05; A01K 2217/07; A01K 2227/30; A01K 2267/01; C07K 16/00; C07K 2317/14; C07K 2317/56; C12N 5/0635; C12N 15/8509
USPC .......... 800/13, 19, 6; 435/349, 328
See application file for complete search history.

(56) References Cited

U.S. PATENT DOCUMENTS

| | | | | |
|---|---|---|---|---|
| 8,592,644 B2 * | 11/2013 | Harriman | ........... | C12N 15/8509 800/19 |
| 9,404,125 B2 * | 8/2016 | Harriman | ............... | C07K 16/00 |
| 9,549,538 B2 * | 1/2017 | Harriman | ............... | C12P 21/02 |
| 10,172,334 B2 * | 1/2019 | Harriman | ........... | C12N 15/8509 |
| 10,687,519 B2 * | 6/2020 | Harriman | ........... | C12N 15/8509 |
| 11,033,009 B2 * | 6/2021 | Harriman | ........... | C07K 16/46 |
| 11,337,409 B2 * | 5/2022 | Leighton | ............. | C12N 5/0635 |
| 2013/0096020 A1 | 4/2013 | Throsby et al. | | |
| 2014/0041067 A1 | 2/2014 | Bradley et al. | | |
| 2014/0317766 A1 * | 10/2014 | Logtenberg | ............ | C07K 16/00 800/18 |
| 2016/0304585 A1 * | 10/2016 | Harriman | ........... | A01K 67/0275 |
| 2017/0107484 A1 | 4/2017 | Macdonald et al. | | |
| 2018/0244804 A1 | 8/2018 | Macdonald et al. | | |

FOREIGN PATENT DOCUMENTS

| | | | |
|---|---|---|---|
| WO | WO 2009/157771 A2 | | 12/2009 |
| WO | 2013/033406 | * | 3/2013 |
| WO | WO 2013/033406 A2 | | 3/2013 |
| WO | WO 2017/035274 A1 | | 3/2017 |

OTHER PUBLICATIONS

"Antiserum." Merriam-Webster.com Dictionary, Merriam-Webster, https://www.merriam-webster.com/dictionary/antiserum. Accessed Dec. 28, 2021.*

(Continued)

*Primary Examiner* — Anne Marie S Wehbe
(74) *Attorney, Agent, or Firm* — James S. Keddie; Bozicevic, Field & Francis LLP

(57) ABSTRACT

This disclosure provides, among other things, strategies for minimizing antibody diversification in a transgenic animal that uses gene conversion for antibody diversification. In some embodiments, the animal may comprise a genome comprising an endogenous immunoglobulin light chain locus comprising: (a) a functional immunoglobulin light chain gene comprising a nucleic acid encoding a light chain variable region; and (b) a plurality of pseudogenes that are operably linked to the functional immunoglobulin light chain gene and that donate, by gene conversion, nucleotide sequence to the nucleic acid encoding a light chain variable region, wherein the pseudogenes are upstream or downstream of the functional immunoglobulin light chain gene and encode the same amino acid sequence as the light chain variable region of the functional immunoglobulin light chain gene of (a). In other embodiments, the locus may have a tandem array of coding sequences for the light chain.

19 Claims, 22 Drawing Sheets

Specification includes a Sequence Listing.

(56) References Cited

OTHER PUBLICATIONS

Harris et al.,"Sequence-Based Discovery Demonstrates That Fixed Light Chain Human Transgenic Rats Produce a Diverse Repertoire of Antigen-Specific Antibodies", Frontiers in Immunology, 2018; 9(889): 1-11.

Kathryn et al., "Common light chain chickens produce human antibodies of high affinity and broad epitope coverage for the engineering of bispecifics", MABS, Jan. 25, 2021, 13(1): e1862451 (11 pages).

* cited by examiner

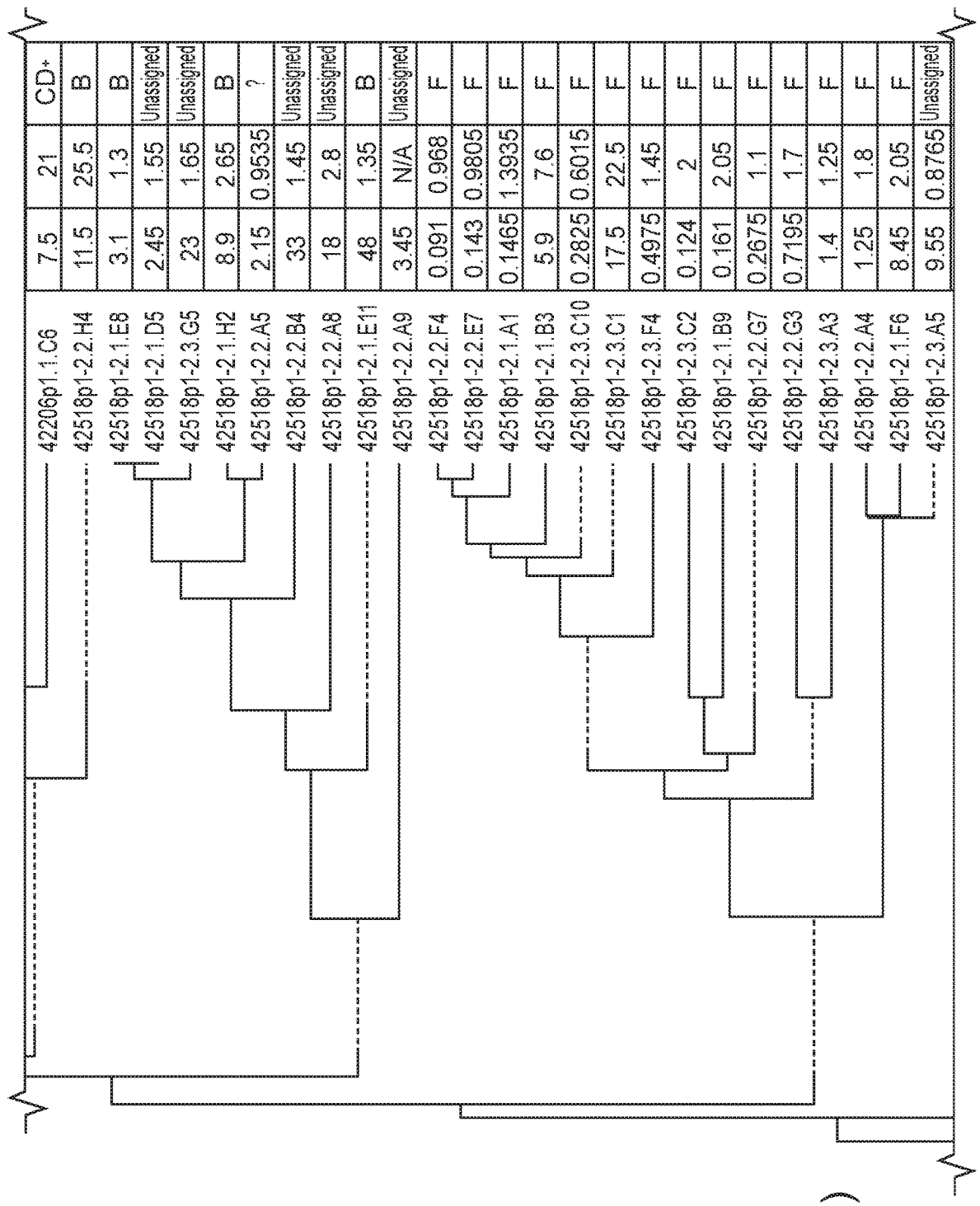
FIG. 11 (Cont. 1)

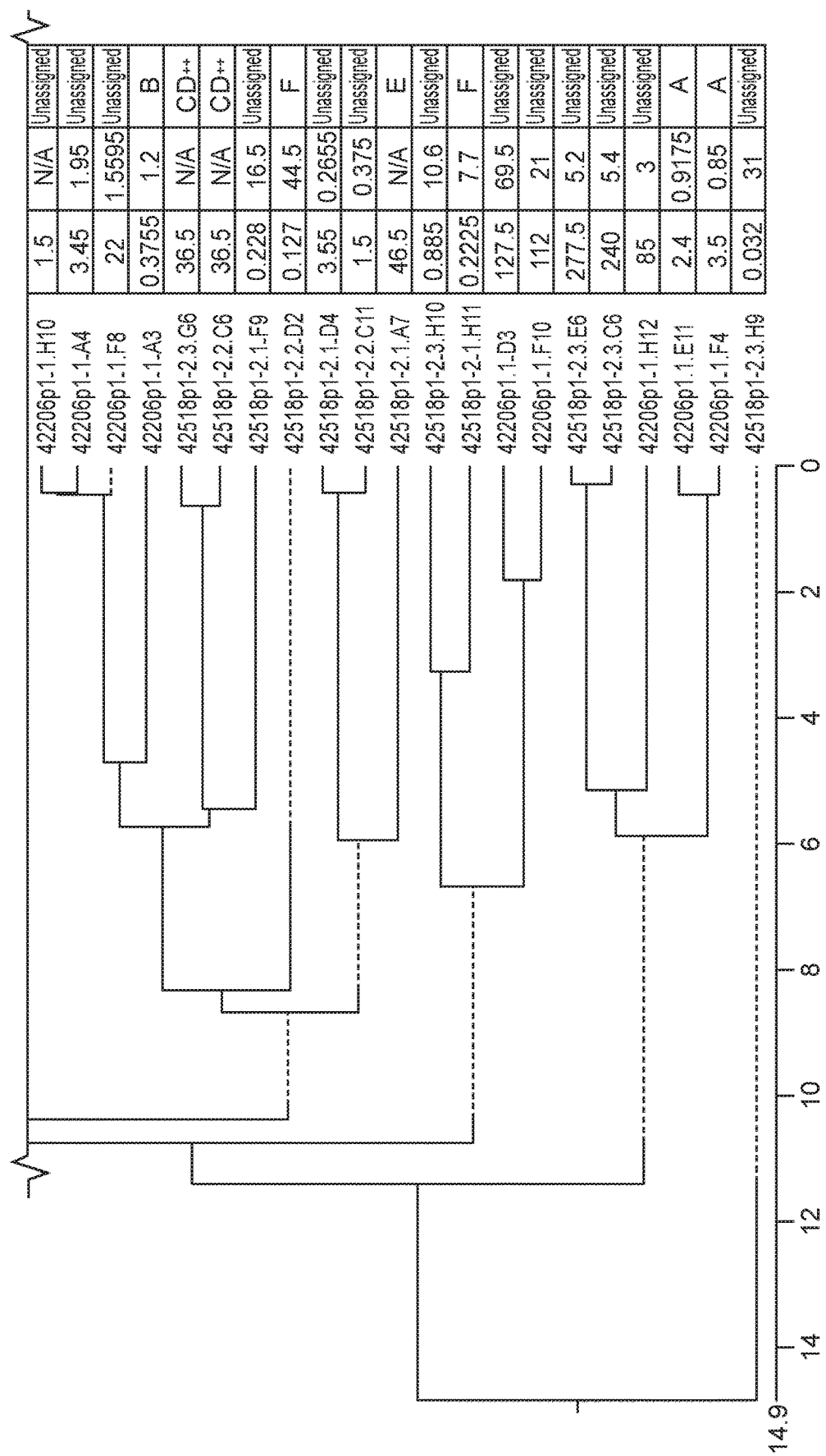
FIG. 11 (Cont. 2)

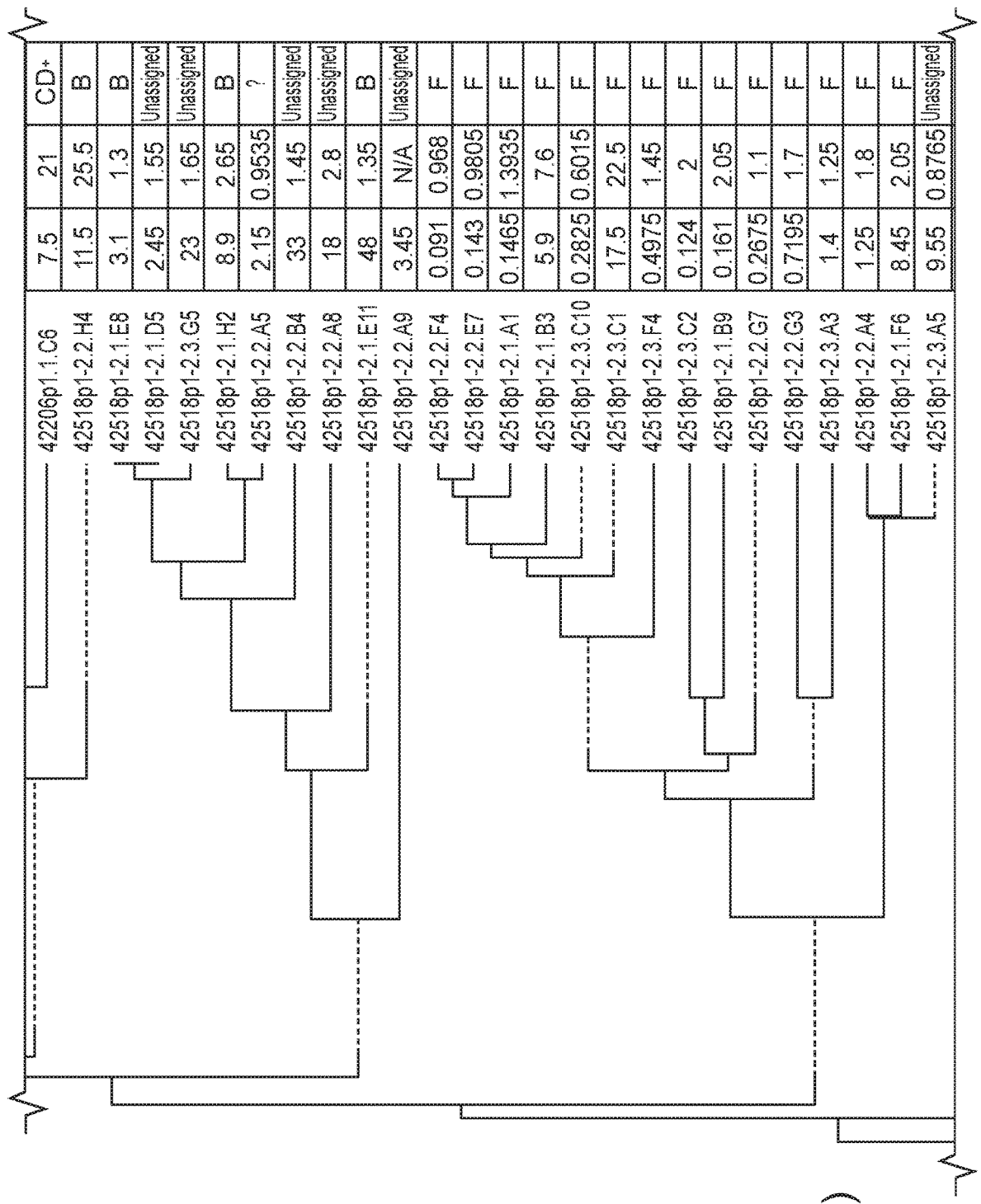
FIG. 20 (Cont. 1)

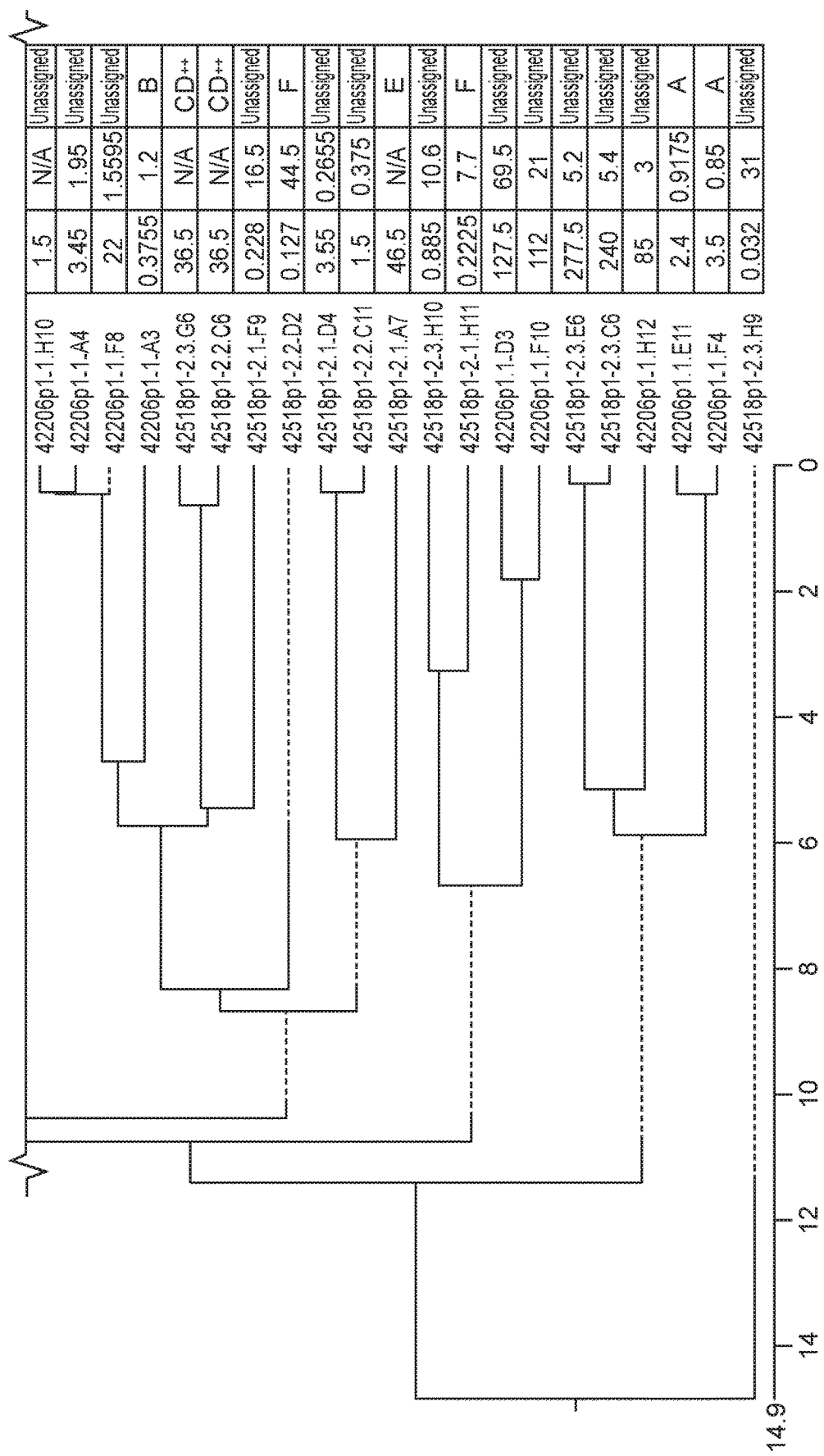
FIG. 20 (Cont. 2)

TRANSGENIC ANIMAL FOR PRODUCING DIVERSIFIED ANTIBODIES THAT HAVE THE SAME LIGHT CHAIN I

CROSS-REFERENCING

This application is a continuation of U.S. application Ser. No. 15/734,187, filed on Dec. 1, 2020, which is the national phase under 35 U.S.C. § 371 of International Application No. PCT/US2019/035526, filed on Jun. 5, 2019, which claims the benefit of U.S. provisional application Ser. No. 62/682,651, filed on Jun. 8, 2018, and 62/684,529, filed on Jun. 13, 2018, which applications are incorporated herein by reference.

BACKGROUND

Classical antibodies are composed of two identical heavy-chains, each of which forms a heterodimer with a common light-chain. In contrast, bispecific antibodies can have two different heavy-chains and two different light-chains and each pair will bind a different antigen. Random association of two different light-chains and two different heavy-chains produces a mixture of many combinations of the component chains. As such, there is a need for approaches that produce antibodies that all have the same light chain.

One of the challenges of producing so-called "common light chain" animals, i.e., animals that produce antibodies that all contain the same light chain, is that somatic hypermutation often changes the light chain variable region coding sequence during affinity maturation in B cells. As such, animals that are engineered to contain a single light chain sequence at the endogenous light chain locus still produce antibodies that have a diversified light chain.

Certain aspects of this disclosure relate to a transgenic animal that produces a common light-chain and use the same for the production of bispecific antibodies.

SUMMARY

This disclosure provides, among other things, two strategies to reduce light chain diversity in an animal that uses gene conversion for antibody diversification. These strategies, which involve making changes to the immunoglobulin light chain locus, can be used alternatively or in combination to produce animals that produce polyclonal antisera in which the light chain is less diverse than equivalent animals that do not have such changes.

In some embodiments, the animal may comprise a genome comprising an immunoglobulin light chain locus comprising: (a) a functional immunoglobulin light chain gene comprising a nucleic acid encoding a light chain variable region; and (b) a plurality of pseudogenes that are operably linked to the functional immunoglobulin light chain gene and that donate, by gene conversion, nucleotide sequence to the nucleic acid encoding a light chain variable region, wherein the pseudogenes are upstream or downstream of the functional immunoglobulin light chain gene and encode the same amino acid sequence as the light chain variable region of the functional immunoglobulin light chain gene of (a).

In B cells of such animals, the light chain variable region coding sequence may become diversified by somatic hypermutation. However, in these embodiments the pseudogenes should repair many of the mutations by gene conversion, thereby restoring the coding sequence for the variable region back to its original form. In these transgene animals, the pseudogenes are essentially performing the opposite function to their normal role in the sense that they are decreasing sequence diversity in the transgenic animals. In wild type animals, the pseudogenes increase sequence diversity.

Such animals produce a polyclonal antiserum in which the light chain is less diverse than equivalent animals that do not have such pseudogenes.

Alternatively or in addition to the above, the transgenic animal may comprise a genome comprising an endogenous immunoglobulin light chain locus comprising a functional immunoglobulin light chain gene comprising a tandem array of antibody coding sequences, wherein each of the nucleic acids in the tandem array encodes a light chain variable domain and a constant region and is operably linked to a promoter, and wherein each coding sequence in the array encodes the same amino acid sequence. The light chains produced in such animals are therefore encoded by several different coding sequences that initially (i.e., before somatic hypermutation, etc.) are identical to one another. The tandem array of coding sequences dilutes the effect of somatic hypermutation in B cells of such an animal. Such animals produce a polyclonal antiserum in which the light chain is less diverse than equivalent animals that do not have a tandem array of antibody coding sequences. The present strategies find use in the production of a diversified population of antibodies that have a so-called "common light chain", i.e., a diversified population of antibodies that all have the same or almost the same light chain variable region, where the light chain light chain variable regions of such antibodies play a passive role in determining binding specificity of the antibodies but nevertheless need to be present for correct folding and secretion. In these cases, the light chain for an antibody can be pre-selected prior to making the transgenic animals. For example, in some cases, the animal may be engineered to produce a diversified population of antibodies that have a common light chain variable region encoded by the human germline, thereby ensuring that at least the light chain of an antibody that contains the common light chain variable region should be well tolerated immunologically when it is administered to a human. In particular, such light chains can be used in bi-specific antibodies have two binding specificities. In these embodiments, both arms of a bi-specific antibody have the same light-chain (i.e., the common light chain) and different heavy chains (which largely determine the binding specificity of the arm).

BRIEF DESCRIPTION OF THE DRAWINGS

The skilled artisan will understand that the drawings, described below, are for illustration purposes only. The drawings are not intended to limit the scope of the present teachings in any way.

DEFINITIONS

Figure 1:
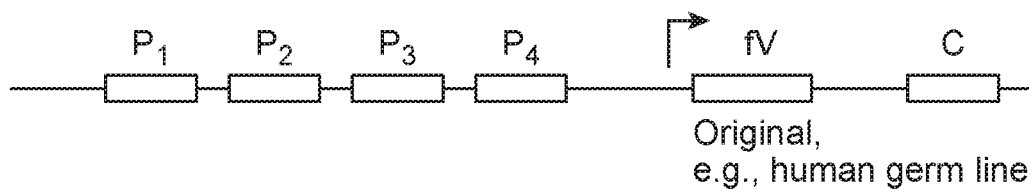
FIG. 1 schematically illustrates an immunoglobulin light chain locus comprising (a) a functional immunoglobulin light chain gene comprising a nucleic acid encoding a light chain variable region ("fV") and (b) a plurality of pseudogenes ($P_1$-$P_4$) that are operably linked to the functional immunoglobulin light chain gene (fV) and that donate, by gene conversion, nucleotide sequence to the nucleic acid encoding a light chain variable region, wherein the pseudogenes are upstream or downstream of the functional immunoglobulin light chain gene and encode the same amino acid sequence as the light chain variable region of the functional immunoglobulin light chain gene.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

The term "nucleic acid" encompasses DNA, RNA, single stranded or double stranded and chemical modifications thereof. The terms "nucleic acid" and "polynucleotide" are used interchangeably herein.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. "Unlinked" means that the associated genetic elements are not closely associated with one another and the function of one does not affect the other.

The term "homozygous" indicates that identical alleles reside at the same loci on homologous chromosomes. In contrast, "heterozygous" indicates that different alleles reside at the same loci on homologous chromosomes. A transgenic animal may be homozygous for a transgene, or hemizygous for a transgene if there is no counterpart at the same locus on the homologous chromosome.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introducing" in the context of inserting a nucleic acid sequence into a cell, includes "transfection" and "transformation" and all other methods of introducing a nucleic acid into a cell, where the nucleic acid sequence may be incorporated into the genome of the cell (e.g., chromosome, plasmid, plastid, or mitochondrial DNA) or converted into an autonomous replicon, or transiently expressed.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The term "replacing", in the context of replacing one genetic locus with another, refers to a single step protocol or multiple step protocol.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "introduced" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

As used herein, the term "isolated", with respect to a cell, refers to a cell that is cultured in vitro. If an animal is described as containing isolated cells, then those isolated cells were cultured in vitro and then implanted into the animal.

The term "progeny" or "off-spring" refers to any and all future generations derived and descending from a particular animal or cell. Thus, the progeny an animal of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell. A chimeric animal may have cells donated by another animal in the germline, in which case the progeny of the animal may be heterozygous for chromosomes in the donated cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The phrases "hybrid animal", "transgenic hybrid animal" and the like are used interchangeably herein to mean an animal obtained from the mating of a first animal having certain qualities with a second animal having certain qualities. For example, a hybrid animal of the present disclosure can refer to the transgenic progeny obtained from the mating of a transgenic first animal that produces a common light-chain with a second transgenic animal that produces a synthetic heavy-chain. A hybrid animal can be immunized and used as a source for the production of antigen-specific antibodies.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')2, and or other antibody fragments that retain specific binding to antigen, and monoclonal antibodies.

Antibodies may exist in a variety of other forms including, for example, Fv, Fab, and (Fab')2, as well as bifunctional (i.e. bispecific) hybrid antibodies (e.g., Lanzavecchia and Scheidegger, Eur. J. Immunol. 1987, 17(1):105-111) and in single chains (e.g., Huston et al., Proc. Natl. Acad. Sci. U.S.A. 1988, 85(16):5879-5883 and Bird et al., Science. 1988, 242(4877):423-426, which are incorporated herein by reference). (See, generally, Hood et al., "Immunology", Benjamin, N.Y., 2nd ed. 1984, and Hunkapiller and Hood, Nature. 1986, 323(6083):15-16).

Chimeric antibodies are antibodies whose light and heavy chain genes have been constructed, typically by genetic engineering, from antibody variable and constant region genes belonging to different species. For example, the variable segments of the genes from a chicken or rabbit monoclonal antibody may be joined to human constant segments, such as gamma 1 and gamma 3. An example of a therapeutic chimeric antibody is a hybrid protein composed of the variable or antigen-binding domain from a chicken or rabbit antibody and the constant or effector domain from a human antibody (e.g., the anti-Tac chimeric antibody made by the cells of A.T.C.C. deposit Accession No. CRL 9688), although other mammalian species may be used.

The term "pseudogene" is used to describe an untranscribed nucleic acid region that contains an open reading frame that may or may not contain a start and/or a stop codon. An amino acid sequence may be "encoded" by a pseudogene in the sense that the nucleotide sequence of the open reading frame can be translated in silico to produce an amino acid sequence. In the context of the heavy and light chain immunoglobulin loci, pseudogenes do not contain promoter regions, recombination signal sequences or leader sequences.

The terms "upstream" and "downstream" are used with reference to the direction of transcription.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between an antibody and analyte when they are specifically bound in an antibody/analyte complex is characterized by a KD (dissociation constant) of less than $10^{-6}$ M, less than $10^{-7}$ M, less than $10^{-8}$ M, less than $10^{-9}$ M, less than $10^{-10}$ M, less than $10^{-11}$ M, or less than about $10^{-12}$ M.

A "variable region" of a heavy or light antibody chain is an N-terminal mature domain of the chain that contains CDR1, CDR2 and CD3, and framework regions (where CDR refers to "complementarity determining region"). The heavy and light chain of an antibody both contains a variable domain. All domains, CDRs and residue numbers are assigned on the basis of sequence alignments and structural knowledge. Identification and numbering of framework and CDR residues is as described in by Chothia et al. and others (Chotia et al., *J. Mol. Biol.* 1998, 278(2):457-479).

VH is the variable domain of an antibody heavy chain. VL is the variable domain of an antibody light chain.

The terms "gene" and "locus" are used interchangeably herein. Neither term implies that a gene is actively transcribed or intact. Both terms encompass genes that have been inactivated.

As used herein, a "chimeric" chicken is a chicken containing a significant number of genetically distinct cells from at least two sources. A chimeric animal may be made by implanting cells from one animal into an embryo of another animal, or by implanting cultured cells (that, e.g., have a modified genome) into an embryo. The implanted cells may be harvested from a culture prior to incorporation into the host embryo. The embryo develops into an animal, and the resultant animal may contain cells from the host as well as the implanted cells. If the donated cells contain an exogenous nucleic acid (i.e., nucleic acid that is not endogenous to the cells), the progeny of the chimeric animal may be "transgenic", where a "transgenic" animal is an animal made up cells containing foreign nucleic acid (i.e., recombinant nucleic acid that is not native to the animal). The foreign nucleic acid molecule may be called a "transgene" herein.

The term "inactivated" is intended to indicate a gene that is not expressed in the sense that the protein encoded by the gene is not expressed. Genes can be inactivated by removing a portion of a coding sequence and/or regulator sequence of a gene. A gene that is disrupted, e.g., "knockout", is a type of inactivated gene. A locus that once contained an expressed endogenous sequence that has since been replaced by a human immunoglobulin sequence that is also expressed contains an inactivated endogenous gene. As such, a locus that contains an expressed human immunoglobulin sequence can have an inactivated endogenous immunoglobulin gene if the endogenous immunoglobulin gene was replaced by the human immunoglobulin sequence. In many case this may be done by knocking out the endogenous sequence (e.g., by deletion of at least part of the sequence) and then inserting the human immunoglobulin sequence at a position that was once occupied by the endogenous sequence.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "genetically linked" refers to two genetic elements that exist on the same chromosome such that there is a tendency for the genetic elements to be inherited together during meiosis (i.e., the elements have a recombination frequency of less than 50%, less than 40%, less than 30%, less than 20%, less than 10% or less than 5%). Two genetic elements that are linked closely to each other are less likely to be separated onto different chromatids during chromosomal crossover events (or "recombination"). The chance that two genetically linked elements become separated during recombination depends on the amount of sequence between the two elements, and can be calculated into a percentage of likelihood, termed "recombination frequency".

As used herein, the term "common light-chain" or "common immunoglobulin light-chain" refers to a light chain variable region that can pair with multiple heavy chain variable regions to produce antibodies that bind to different antigens. The common light chain is a passive partner for antigen binding, and antigen binding is determined by the heavy chains. For example, bi-specific antibodies have two binding specificities and, in some cases, both arms of a bi-specific antibody have the same light-chain (i.e., a "common" light chain) and different heavy chains (which largely determine the binding specificity of the arm).

A common light-chain of the present disclosure comprises a "pre-rearranged light-chain variable region" (or "pre-rearranged variable region"), wherein the light-chain variable region has a defined sequence and has been selected for properties that allows it to pair well with multiple heavy chain variable regions to produce antibodies of different specificities. A "common light-chain transgene" of the present disclosure may be a transgene that at least comprises a common light-chain coding sequence (or pre-rearranged light-chain variable region) and a light-chain constant region in one long open reading frame. This transgene may be a cDNA.

As used herein, the term "functional" is intended to mean that the region is transcribed and translated by the cell.

As used herein, the terms "less diversified", "less diverse", "reduced diversification" and equivalents thereof are intended to mean that the light chain variable region of at least 50% of the antibodies produced by the animal that are specific for the antigen used to immunize the animal (i.e., the majority of the antigen-specific antibodies that have different sequences, e.g., at least 80% or at least 90% of the antigen-specific antibodies) have an amino acid sequence that is either identical to the variable region encoded by the functional immunoglobulin light chain gene or a modified version of that sequence that has up to 5 amino acid substitutions (1, 2, 3, 4 or 5 substitutions). For example, the light chain variable region of some the antibodies produced by the animal will have an amino acid sequence that is the same as the variable region encoded by the functional immunoglobulin light chain gene, some will have an amino acid sequence that is identical to the variable region encoded by the functional immunoglobulin light chain gene except for one amino acid substitution, some will have an amino acid sequence that is identical to the variable region encoded by the functional immunoglobulin light chain gene except for two amino acid substitutions, some will have an amino acid sequence that is identical to the variable region encoded by the functional immunoglobulin light chain gene except for three amino acid substitutions, some will have an amino acid sequence that is identical to the variable region encoded by the functional immunoglobulin light chain gene except for four amino acid substitutions, some will have an amino acid sequence that is identical to the variable region encoded by the functional immunoglobulin light chain gene except for five amino acid substitutions, where the total number of antibodies that have the same amino acid sequence as the variable region encoded by the functional immunoglobulin light chain gene with the exception of up to 5 amino acid substitutions represent the majority of the different antigen-specific antibodies produced by the animal (at least 50%, at least 80% or at least 90% of the antigen-specific antibodies). The remainder of the antibodies (i.e., those that contain 6 or more, 7 or more or 8 or more amino acid substitutions are in the minority).

Further definitions may be found elsewhere in this disclosure.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, a transgenic animal is provided. In certain embodiments, the animal may be any non-human animal that has a relatively small number of light chain genes, or an animal that employs gene conversion for developing their primary antigen repertoire and, as such, the animal may be any of a variety of different animals. In one embodiment, the animal may be a bird, e.g., a member of the order Galliformes such as a chicken or turkey, or a member of the order Anseriformes such as a duck or goose, or a mammal, e.g., a lagamorph such as rabbit, or a farm animal such as a cow, sheep, pig or goat.

Some of this disclosure relates to a transgenic chicken containing one or more transgenes. Since the nucleotide sequences of the immunoglobulin loci of many animals are known, as are methods for modifying the genome of such animals, the general concepts described below may be readily adapted to any suitable animal, particularly animals that employ gene conversion for developing their primary antigen repertoire. The generation of antibody diversity by gene conversion between the variable region of a transcribed immunoglobulin heavy or light chain gene and operably linked (upstream) pseudo-genes that contain different variable regions is described in a variety of publications such as, for example, Butler (Rev. Sci. Tech. 1998 17: 43-70), Bucchini (Nature 1987 326: 409-11), Knight (Adv. Immunol. 1994 56: 179-218), Langman (Res. Immunol. 1993 144: 422-46), Masteller (Int. Rev. Immunol. 1997 15: 185-206), Reynaud (Cell 1989 59: 171-83) and Ratcliffe (Dev. Comp. Immunol. 2006 30: 101-118). See also US20110055938.

Figure 2:
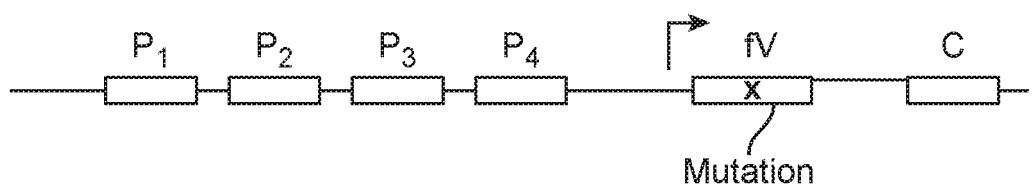
FIG. 2 schematically illustrates how mutations in the functional immunoglobulin light chain (fV) can be repaired by the pseudogenes ($P_1$-$P_4$) via gene conversion.
Figure 2:
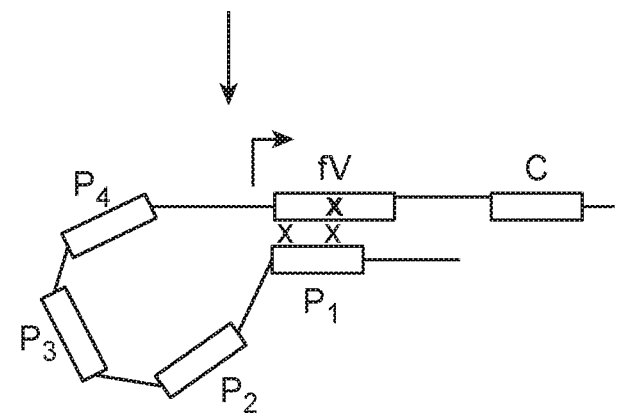
Figure 2:
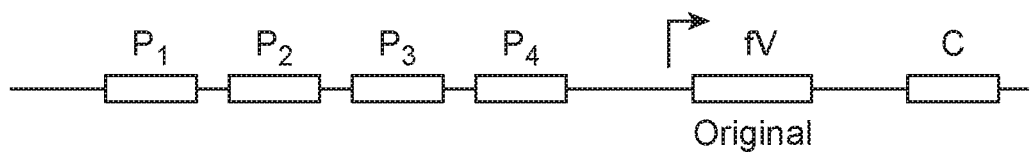

Provided herein, among other things, is a transgenic animal that uses gene conversion for antibody diversification (e.g., a transgenic chicken) comprising a genome comprising an endogenous immunoglobulin light chain locus comprising: (a) a functional immunoglobulin light chain gene comprising a nucleic acid encoding a light chain variable region (i.e., a "functional V region"); and (b) a plurality of pseudogenes that are operably linked to the functional immunoglobulin light chain gene and that donate, by gene conversion, nucleotide sequence to the nucleic acid encoding the light chain variable region, wherein the pseudogenes are upstream or downstream of the functional immunoglobulin light chain gene and encode the same amino acid sequence as the light chain variable region of the functional immunoglobulin light chain gene of (a). In other words, the sequences encoded by the functional gene and the pseudogenes are the same so that any mutations in the variable region encoded by the functional gene can be repaired by the pseudogenes via gene conversion. In some embodiments, the pseudogenes may contain nucleotide sequences that are identical or near identical to at least part of (e.g., at least 50%, at least 80% of or at least 90% of) the nucleic acid encoding a light chain variable region in the functional gene. However, the degeneracy of the genetic code allows the same amino acid sequence to be encoded by different sequences of nucleotides. As such, in some embodiments, the pseudogenes may contain nucleotide sequences that are near identical to at least part of the nucleic acid encoding a light chain variable region in the functional gene. In these embodiments, the amino acid sequences encoded by the sequences should be the same and their sequence identity should be sufficient for gene conversion to occur. In these embodiments, the nucleotide sequence of the pseudogenes should be at least 90% identical (e.g., at least 95% identical) to the coding sequence for the variable region of the functional gene. This embodiment is illustrated in FIG. 1. FIG. 2 illustrates how mutations in the functional V region can be repaired by the pseudogenes via gene conversion.

In some embodiments, the nucleic acid encoding the light chain variable region of (a) may comprise a variable (V) segment and a joining (J) segment. In these embodiments, the light chain variable region of (a) may be encoded by a human germline light chain V segment and a human germline light chain J segment. In other words, the sequences encoded by the V and J segments should be human germline sequences. In these embodiments, the V segment of the light chain variable region of (a) may be encoded by a germline light chain kappa V segment or a germline light chain lambda V segment. In these embodiments, the pseudogenes may encode at least part of the same amino acid sequence as the V segment. In some cases, the pseudogenes may encode at least part of the same amino acid sequence as the V and J segments. The light chain variable region may be from a human monoclonal antibody. As shown in FIGS. 1 and 2, the C region may be encoded by a separate exon. However, in some embodiments, the light chain C region may be in the same open reading frame as the V and J segments.

In some embodiments, the pseudogenes are less than 400 nt in length, e.g., 200-400 nucleotides in length or 300-400 nucleotides in length. In some embodiments, there are up to 30 of the pseudogenes, e.g., up to 20 or up to 10.

The transgenic animal may be heterozygous or homozygous for the immunoglobulin light chain locus.

A method comprising (a) immunizing a transgenic animal with an antigen; and (b) obtaining from the animal an antibody that specifically binds to the antigen is also provided. The antibody may be monoclonal or polyclonal. In some embodiments, the method may further comprise (c) making hybridomas using B cells of the transgenic animal; and (d) screening the hybridomas to identify a hybridoma that produces an antibody that specifically binds to the antigen. Alternatively B cells can be screened without making hybridomas. This method may comprise using PCR to amplify at least the heavy chain variable region-encoding nucleic acid from B cells of the transgenic animal, and expressing a recombinant antibody using the amplified nucleic acid. The light chain sequence should be known already and does not need to be sequenced.

Also provided is a polyclonal antibody produced by a transgenic animal, wherein at least 50% (e.g., at least 60%, at least 70%, at least 80%, or at least 90%) of the antibodies in the antiserum have substantially the same light chain sequence (e.g., light chain variable domains that are at least 90%, at least 95, or at least 98% as one another or contain up to five (i.e., 0, 1, 2, 3, 4 or 5) amino acid substitutions relative to the functional V region coding sequence). Also provided is a population of at least 100 B cells (e.g. 1,000, 10,000 or 100,000 B cells) produced by a transgenic animal, wherein the B cell produce antibodies that bind to different epitopes and wherein the light chains produced by at least 50% (e.g., at least 60%, at least 70%, at least 80%, or at least 90%) of the B cells have substantially the same light chain sequence (e.g., light chain variable domains that are at least 90%, at least 95, or at least 98% as one another or contain up to five (i.e., 0, 1, 2, 3, 4 or 5) amino acid substitutions relative to the functional V region coding sequence).

The heavy chain locus of the animal may be wild type, or it may have been modified. In some embodiments, the heavy chain locus may produce a heavy chain that is composed of human sequences (see, e.g., PCT/US19/20799, filed on Mar. 5, 2019, 2018, and incorporated by reference), e.g., human germline sequence. For example, the heavy chain locus may contain a functional human VH sequence and VH pseudogenes, where the VH pseudogenes diversify the function human VH sequence via gene conversion. In some embodiments, the transgenic animal may have a genome that further comprises a "synthetic" immunoglobulin heavy chain (IgH) locus ("SynV") comprising: a) a functional IgH gene comprising a nucleic acid encoding a heavy chain variable region comprising: i) a heavy chain CDR1, CDR2 and CDR3 regions; and ii) a heavy chain framework; and b) a plurality of pseudogenes that encode heavy chain variable regions each comprising: i) heavy chain CDR1, CDR2 and CDR3 regions; and ii) a heavy chain framework region that is identical in amino acid sequence to the heavy chain framework of a) (ii); wherein the recombinant IgH locus comprises: in operable linkage: an intron region, a constant domain region-encoding region and a 3' untranslated region; wherein at least part of the intron region is endogenous to the genome of the transgenic animal; and the nucleic acid of a) and pseudogene of b), are exogenous to the genome of the transgenic animal, and wherein the plurality of pseudogenes are operably linked to the functional IgH gene and donate nucleotide sequences to the nucleic acid of a) by gene conversion in the transgenic animal; and wherein the transgenic animal expresses a recombinant immunoglobulin comprising a diversified form of the functional IgH variable region. The animal may be homozygous or heterozygous for the modified heavy chain locus.

In some embodiments, the coding sequence in the functional V region may encode immunoglobulin light-chain comprising a pre-rearranged variable region or a cDNA.

As shown in the figures, the light chain locus comprises a functional immunoglobulin light chain gene that is expressed (i.e., transcribed to produce an mRNA that is subsequently translated) to produce a light chain of an antibody, and, operably linked to (which, in the case is chicken and many other species is immediately upstream of) the functional light chain gene, a plurality of different pseudogene light chain variable regions, where the variable regions of the pseudogenes are operably linked to the functional immunoglobulin light chain in that they the alter the sequence of the functional immunoglobulin light chain gene by gene conversion (i.e., by substituting a sequence of the functional immunoglobulin light chain gene variable region with a sequence of a pseudogene variable region). In the transgenic animal, gene conversion between the functional immunoglobulin light chain gene variable region and a pseudogene variable region alters the sequence of the functional immunoglobulin light chain gene variable region by as little as a single codon up to the entire length of the variable region. In certain cases a pseudogene variable region may donate the sequence of at least one CDR (e.g., CDR1, CDR2 or CDR3) from a pseudogene variable region in to the variable region of the functional gene. The light chains of the antibodies produced by the transgenic animal are therefore encoded by whatever sequence is donated from the pseudogene variable regions into the variable region of the functional light chain gene. Since the variable regions encoded by the pseudogene are the same as one another and the same as the variable region of the functional light chain gene, gene conversion repairs many of the mutations that are made in B cells during, e.g., affinity maturation.

Likewise, the transgenic animal may also contain an a functional immunoglobulin heavy chain gene that is transcribed and translated to produce a heavy chain of an antibody, and, operably linked to (e.g., immediately upstream of) the functional heavy chain gene, a plurality of different pseudogene heavy chain variable regions, where the variable regions of the pseudogenes are operably linked to the functional immunoglobulin light chain in that they alter the sequence of the functional immunoglobulin heavy chain gene by gene conversion. In the transgenic animal, gene conversion between the functional immunoglobulin heavy chain gene variable region and a pseudogene variable region alters the sequence of the functional immunoglobulin heavy chain gene variable region by as little as a single codon up to the entire length of the variable region. In certain cases may a pseudogene variable region may donate the sequence of at least one CDR (e.g., CDR1, CDR2 or CDR3) from a pseudogene variable region to the variable region of the functional gene. The heavy chains of the antibodies produced by the transgenic animal are therefore encoded by whatever sequence is donated from the pseudogene variable regions into the variable region of the functional heavy chain gene.

The antibodies produced by the transgenic animal are therefore encoded by whatever sequences are donated from the pseudogene variable regions to the variable region of the functional gene. Since different sequences are donated in different cells of the animal, the antibody repertoire of the animal is determined by which sequences are donated from the pseudogene variable regions to the variable region of the functional gene.

In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, the light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6. See PCT WO 2005/005604 for a description of the different germline sequences.

In some embodiments, the nucleotide sequence and/or amino acid sequence of the introduced transcribed variable region may be human, i.e., may contain the nucleotide and/or amino acid sequence of a human antibody or germline sequence. In these embodiments, both the CDRs and the framework may be human. In other embodiments, the nucleotide sequence and/or amino acid sequence of the introduced transcribed variable region is not human and may instead be at least 80% identical, at least 90% identical, at least 95% or more identical to a human sequence. For example, relative to a human sequence, the introduced transcribed variable region may contain one or more nucleotide or amino acid substitution.

In particular embodiments, part of the light chain locus that includes the constant domain-encoding region, part of an intron, and the 3'UTR of the functional gene may be endogenous to the animal and the remainder of the light chain locus, including the variable regions of the functional gene, the remainder of the intron and the pseudogenes may be exogenous to the animal, i.e., made recombinantly and introduced into the animal proximal to the constant domain, part intron and 3' UTR in such a way that a functional light chain gene is produced and the pseudogenes are capable of donating sequence to the functional light chain gene by gene conversion. In certain cases the light chain locus of the animal may contain, in operable linkage: an intron region, a constant domain-encoding region and a 3' untranslated region; where the intron region, the constant domain-encoding region and the 3' untranslated region are endogenous to the genome of the transgenic animal and a plurality of pseudogene light chain variable regions, where the plurality of pseudogene light chain variable regions are exogenous to the genome of the transgenic animal. The constant domain encoding region can be human or it can be exogenous to the genome of the transgenic animal. In other embodiments, the constant region may be encoded in the open reading frame in the functional gene.

Likewise, part of the heavy chain locus, including the constant region, part of an intron region and the 3'UTR of the functional gene, may be endogenous to the animal and the remainder of the heavy chain locus, including the variable domains of the functional gene, the remainder of the intron and the pseudogenes may be exogenous to the animal, i.e., made recombinantly and introduced into the animal proximal to the constant domain, part intron and 3' UTR in such a way that a functional gene is produced and the pseudogenes are capable of donating sequence to the functional gene by gene conversion. In certain cases the heavy chain locus of the animal may contain, in operable linkage: an intron region, a constant domain-encoding region and a 3' untranslated region, where the intron region, the constant domain-encoding region and the 3' untranslated region are endogenous to the genome of the transgenic animal, and a plurality of pseudogene heavy chain variable regions, where the plurality of pseudogene heavy chain variable regions are exogenous to the genome of the transgenic animal.

In certain embodiments, an antibody produced by a subject transgenic animal may contain an endogenous constant domain and variable domains that are exogenous to the animal. Since an endogenous constant region may be employed in these embodiments, the antibody may still undergo class switching and affinity maturation, which allows the animal to undergo normal immune system development, and mount normal immune responses. In specific embodiments transgenic chickens have three endogenous constant regions in the heavy chain locus encoding IgM, IgY and IgA. During the early stages of B cell development, B cells express IgM. As affinity maturation proceeds, class switching converts the constant region into IgY or IgA. IgY provides humoral immunity to both adults and neonatal chicks which receive about 200 mg of IgY via a reserve deposited into egg yolk. IgA is found primarily in lymphoid tissues (eg. the spleen, Peyer's patches and Harderian glands) and in the oviduct. In other embodiments, the constant region may be a human constant region.

The number of introduced pseudogene variable regions present at the light and/or heavy chain locus may vary and, in particular embodiments, may be in the range of 1-50, e.g., 2 to 50 or 10 to 25. In particular embodiments, at least one (e.g., at least 2, at least 3, at least 5, at least 10 or more) of the plurality of pseudogene light chain variable regions may be in reverse orientation relative to the transcribed light chain variable region. Likewise, in particular embodiments, at least one (e.g., at least 2, at least 3, at least 5, at least 10 or more) of the plurality of pseudogene heavy chain variable regions may be in reverse orientation relative to the heavy chain transcribed variable region. In particular embodiments, the plurality of pseudogene variable regions are not in alternating orientations, and in certain cases may contain a series of at least 5 or at least 10 adjacent pseudogene regions that are in opposite orientation relative to the transcribed variable region. In one embodiment, the pseudogene region that is most distal from the transcribed variable region is in the same orientation as the transcribed variable region, and the pseudogene regions between the most distal region and the transcribed variable region are in the reverse orientation relative to the transcribed variable region.

A pseudogene typically contains a sequence of at least 50, at least 100, at least 200 or at least 300 contiguous nucleotides that is at least 80% identical, e.g., at least 85% identical, at least 90% identical or at least 95% identical to sequence in the transcribed region.

ALTERNATIVE EMBODIMENTS

Figure 3:
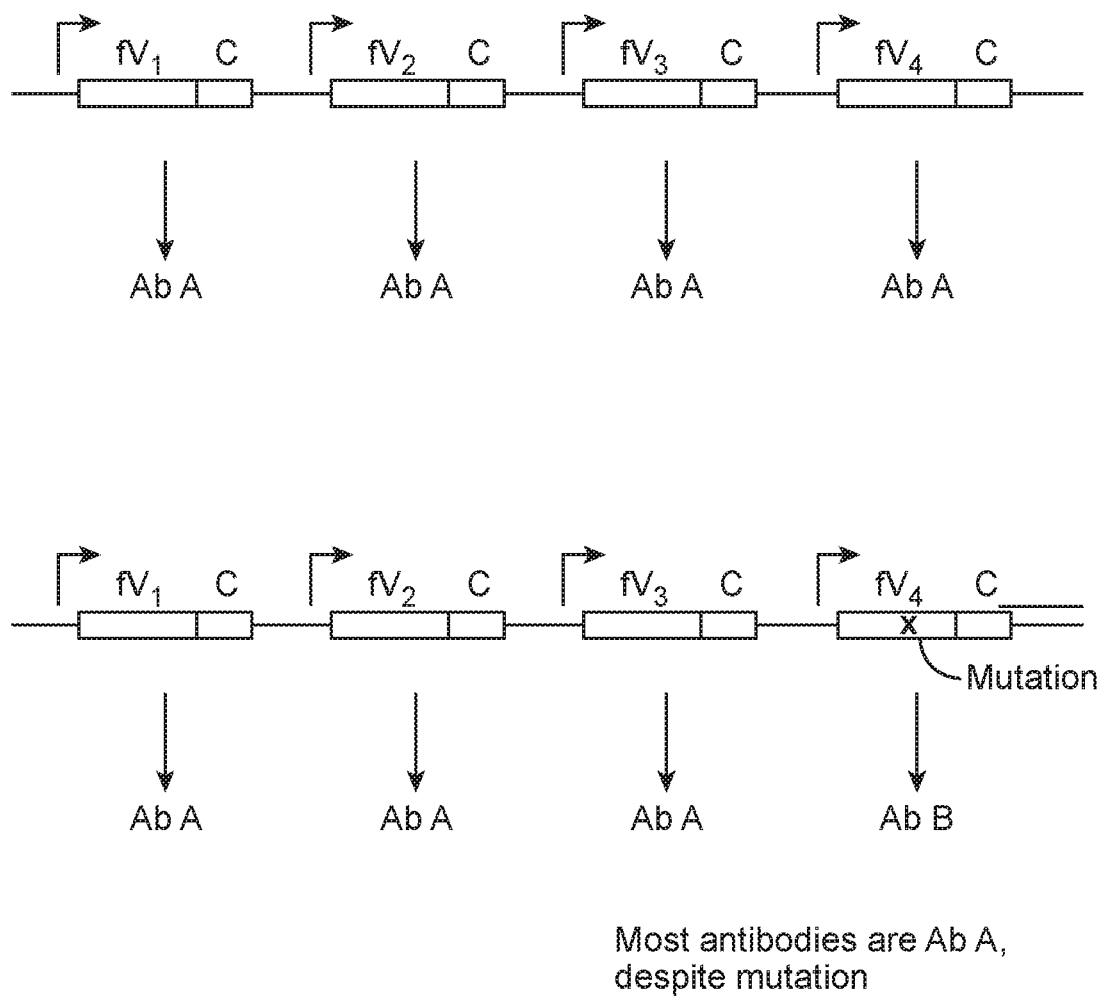
FIG. 3 schematically illustrates an alternative embodiment that can be employed independently or in combination with the embodiment shown in FIGS. 1 and 2 in which diversification of the light chain can be reduced using an array of functional variable regions ($fV_1$-$fV_4$).

Alternative embodiments provide a transgenic animal that uses gene conversion for antibody diversification, comprising a genome comprising an endogenous immunoglobulin light chain locus comprising: a functional immunoglobulin light chain gene comprising a tandem array of antibody coding sequences, wherein each of the nucleic acids in the tandem array encodes a light chain variable domain and a constant region and is operably linked to a promoter, and wherein each coding sequence in the array encodes the same amino acid sequence. This embodiment is schematically illustrated in FIG. 3. In any embodiment, there may be at least 2 (e.g., at least 3, 4, 5, e.g., 5-30) of the coding sequences. In any embodiment, the coding sequence may comprise a prearranged V segment, J segment and C region. In these embodiments, the prearranged V segment, a J segment and C region may all encode human germline antibody sequences. In any embodiment, the light chain variable domain may be from a human monoclonal antibody. In any embodiment, the locus may additionally comprise a plurality of pseudogenes that are operably linked to the functional immunoglobulin light chain gene and that donate, by gene conversion, nucleotide sequence to the tandem array of antibody coding sequences, wherein the pseudogenes are upstream or downstream of the functional immunoglobulin light chain gene and encode the same amino acid sequence as the antibody coding sequences in the tandem array. In any embodiment, the transgenic animal can be a chicken. Options for the various components that can be in this locus and/or the heavy chain locus are described above and below. Methods of use are described below.

In these embodiments, all of the coding sequences should be independently transcribed and translated to produce a corresponding number of full-length light chains (which can be pre-rearranged). Mutations that occur in individual repeats will be diluted out by the other copies, which should not have the same mutations. The pool of light chains expressed in each cell will thus be a mixture of proteins produced by the tandem copies, and no single light chain sequence will be selected during the immune response for functional binding to the target. Light chain produced using this system should be a common light chain.

The above-described transgenic animal may be made by modifying the genome of an animal recombinantly. Methods for producing transgenic animals, e.g., mice and chickens, etc. are known, and, in particular, methods for modifying the genomes of animal that use gene conversion are also known (see, e.g., Sayegh, Vet. Immunol. Immunopathol. 1999 72:31-7 and Kamihira, Adv. Biochem. Eng. Biotechnol. 2004 91: 171-89 for birds, and Bosze, Transgenic Res. 2003 12:541-53 and Fan, Pathol. Int. 1999 49: 583-94 for rabbits and Salamone J. Biotechnol. 2006 124: 469-72 for cow), as is the structure and/or sequence of the germline immunoglobulin heavy and light chain loci of many of those species (e.g., Butler Rev Sci Tech 1998 17:43-70 and Ratcliffe Dev Comp Immunol 2006 30: 101-118), the above-described animal may be made by routine methods given this disclosure. Methods for making transgenic chickens are known. See, e.g., 8,592,644, U.S. Pat. No. 8,889,662, Collarini et al (Poult Sci. 2015 94: 799-803), van de Lavoir (Nature. 2006 441: 766-9) and Schusser et al (Proc Natl Acad Sci USA. 2013 110: 20170-5.

Also provided is a method for producing antibodies that contains a common light-chain. In some embodiments this method may comprise: immunizing a transgenic animal as described above with antigen, and, if the antibodies are polyclonal, the method may comprise isolating the antibodies from a bleed from the animal. If the animal is homozygous for the common light chain sequence, then all of the antibodies in the polyclonal antiserum should have the same light chain. If monoclonal antibodies are desired, then the method may comprise b) making hybridomas using cells of the immunized transgenic animal; c) screening the hybridomas to identify an antigen-specific hybridoma; and d) isolating an antigen-specific antibody from the antigen-specific hybridoma.

In certain embodiments, the animal may be immunized with: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL—related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HERS, HLA-DR, HLA-DR10, HLA ClassII, IgE, GPiib/iiia (integrin), Integrin aVß3, Integrins a4ß1 and a4ß7, Integrin ß2, IFN-gamma, IL-1ß, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFßR (Beta platelet-derived growth factor receptor), PMSA, renal carcinoma antigen G250, RSV, E-Selectin, TGFbeta1, TGF-beta2, TNFα, DR4, DR5, DR6, VAP-1 (vascular adhesion protein 1) or VEGF, or the like in order to produce a therapeutic antibody.

The antigens can be administered to a transgenic host animal in any convenient manner, with or without an adjuvant, and can be administered in accordance with a predetermined schedule.

In any embodiment in which the functional immunoglobulin light chain gene is human, the endogenous pseudogenes can be present or absent. For example, if the functional immunoglobulin light chain gene is composed of human germline sequences then the endogenous chicken pseudogenes can be present or absent. If the endogenous chicken pseudogenes are present they will not contribute any sequence to the functional gene because the sequence identity is too low for gene conversion.

After immunization, serum or milk from the immunized transgenic animals can be fractionated for the purification of pharmaceutical grade polyclonal antibodies specific for the antigen. In the case of transgenic birds, antibodies can also be made by fractionating egg yolks. A concentrated, purified immunoglobulin fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal antibody, antibody-producing cells, e.g., spleen cells, may isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1, U.S. Pat. No. 4,977,081, WO 97/16537, and EP 0 491 057 B1, the disclosures of which are incorporated herein by reference. In vitro production of monoclonal antibodies from cloned cDNA molecules has been described by Andris-Widhopf et al., J Immunol Methods 242:159 (2000), and by Burton, Immunotechnology 1:87 (1995), the disclosures of which are incorporated herein by reference.

If the antibody does not already contain human framework regions, the method may further include humanizing the antibody, which method may include swapping the constant domain of the antibody with a human constant domain to make a chimeric antibody, as well as in certain cases humanizing the variable domains of the antibody by e.g., CDR grafting or resurfacing etc. Humanization can be done following the method of Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/U598/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, including references cited therein.

As such, in addition to the transgenic animal, a method comprising immunizing the transgenic animal with an antigen and obtaining from the transgenic animal an antibody that specifically binds to the antigen is also provided. The method may include making hybridomas using cells of the transgenic animal; and screening the hybridomas to identify a hybridoma that produces an antibody that specifically binds to the antigen. Alternatively B cells can be screened without making hybridomas.

Once monoclonal antibodies that bind to different antigen have been isolated, then bi-specific antibodies can be made using any convenient method. For example, two heavy chain sequences can be expressed in a single host cell along with a single common light chain, in which case a portion of the antibodies secreted by those cells should be bi-specific. Alternatively, two heavy chains and the common light chain may be separately expressed and folded or joined together in vitro.

All of the antibodies produced by this animal should have a light chain which, except for a relatively small number of amino acids substitutions (e.g., 1-5 substitutions) that have not been repaired by gene conversion, should be identical.

The heavy chains variable domain of the antibodies are made "naturally" by the immune system of the animal. Such antibodies may, in certain case, be post-translationally modified (e.g., glycosylated) by the host cell and may have a glycosylation pattern and composition characteristic of the species of transgenic animal.

If needed, an identical strategy can be employed to minimize diversity of the heavy chain in animals. In these embodiments, the animals will contain a functional heavy chain gene and pseudogenes that encode the same sequence as that gene.

The sequences of the antigen-specific binding regions of antibodies produced by the transgenic animal described above should be relatively straightforward to obtain because, if desired, all or any of the coding sequences for a diversified population of heavy chain variable domains can be amplified from cDNA using a single pair of PCR primers. Because the specificity and affinity of each antibody should be solely determined by the amino acid sequence of the heavy chain variable domain, there is no need to identify or sequence the cognate light chain. As such, the amino acid sequences for antigen-specific heavy chain variable domains should be relatively straightforward to obtain. As noted above, in some cases, B cells or hybridomas may be functionally screened in order to select for cells that express antigen-specific heavy chains. Heavy chain variable domain coding sequences may be amplified from an enriched or unenriched population of B cells (e.g., PBMCs) en masse. If sequences are amplified from an unenriched population of B cells, the sequences encoding antigen-specific variable domains should be identifiable because they are more highly expressed than sequences that are not antigen-specific (due to B cell activation) and because they potentially belong to more variable clades. Moreover, because these heavy chains do not need a specific light chain for binding, there is no need to determine which light chain pairs with which heavy chain before performing follow up work.

CLAUSES

Embodiment 1. A transgenic animal that uses gene conversion for antibody diversification, comprising a genome comprising an endogenous immunoglobulin light chain locus comprising: (a) a functional immunoglobulin light chain gene comprising a nucleic acid encoding a light chain variable region; and (b) a plurality of pseudogenes that are operably linked to said functional immunoglobulin light chain gene and that donate, by gene conversion, nucleotide sequence to the nucleic acid encoding a light chain variable region, wherein the pseudogenes are upstream or downstream of the functional immunoglobulin light chain gene and each of the pseudogenes encodes the same amino acid sequence as the light chain variable region of the functional immunoglobulin light chain gene of (a).

Embodiment 2. The transgenic animal of embodiment 1, wherein the pseudogenes contain a nucleotide sequence that is identical to at least part of the nucleic acid encoding a light chain variable region.

Embodiment 3. The transgenic animal of any prior embodiment, wherein the transgenic animal is a chicken.

Embodiment 4. The transgenic animal of any prior embodiment, wherein the nucleic acid encoding the light chain variable region of (a) comprises a variable (V) segment and a joining (J) segment.

Embodiment 5. The transgenic animal of embodiment 4, wherein the light chain variable region of (a) is encoded by a human germline light chain V segment and a human germline light chain J segment.

Embodiment 6. The transgenic animal of embodiment 5, wherein the V segment of the light chain variable region of (a) is encoded by a germline light chain kappa V segment.

Embodiment 7. The transgenic animal of embodiment 5, wherein the V segment of the light chain variable region of (a) is encoded by a germline light chain lambda V segment.

Embodiment 8. The transgenic animal of any of embodiments 4-7, wherein the pseudogenes encode at least part of the same amino acid sequence as the V segment.

Embodiment 9. The transgenic animal of any of embodiments 4-7, wherein the pseudogenes encode at least part of the same amino acid sequence as the V and J segments.

Embodiment 10. The transgenic animal of any prior embodiment, wherein the light chain variable region is from a human monoclonal antibody.

Embodiment 11. The transgenic animal of any prior embodiment, wherein the pseudogenes are less than 400 nt in length.

Embodiment 12. The transgenic animal of any prior embodiment, wherein the pseudogenes are 300-400 nucleotides in length.

Embodiment 13. The transgenic animal of any prior embodiment, wherein there are up to 30 of said pseudogenes.

Embodiment 14. The transgenic animal of any prior embodiment, wherein the transgenic animal is heterozygous for the immunoglobulin light chain locus.

Embodiment 15. The transgenic animal of any prior embodiment, wherein the transgenic animal is homozygous for the immunoglobulin light chain locus.

Embodiment 16. A transgenic animal that uses gene conversion for antibody diversification, comprising a genome comprising an endogenous immunoglobulin light chain locus comprising:
  a functional immunoglobulin light chain gene comprising a tandem array of antibody coding sequences, wherein each of the nucleic acids in the tandem array encodes a light chain variable domain and a constant region and is operably linked to a promoter, and wherein each coding sequence in the array encodes the same amino acid sequence.

Embodiment 17. The transgenic animal of embodiment 16, wherein there are at least 2 (e.g., at least 3, 4, 5, e.g., 5-30) of said coding sequences.

Embodiment 18. The transgenic animal of embodiment 16 or 17, wherein the coding sequence comprise a prearranged V segment, J segment and C region.

Embodiment 19. The transgenic animal of any of embodiments 16-18, wherein the prearranged V segment, a J segment and C region all encode human germline antibody sequences.

Embodiment 20. The transgenic animal of any of embodiments 16-18, wherein the light chain variable domain is from a human monoclonal antibody.

Embodiment 21. The transgenic animal of any of embodiments 16-20, further comprising:
  (b) a plurality of pseudogenes that are operably linked to said functional immunoglobulin light chain gene and that donate, by gene conversion, nucleotide sequence to the tandem array of antibody coding sequences, wherein the pseudogenes are upstream or downstream of the functional immunoglobulin light chain gene and each of the pseudogenes encodes the same amino acid sequence as the antibody coding sequences in the tandem array of (a).

Embodiment 22. The transgenic animal of embodiment 21, wherein the pseudogenes contain a nucleotide sequence that is identical to at least part of the antibody coding sequences.

Embodiment 23. The transgenic animal of embodiment 21 or 22, wherein the transgenic animal is a chicken.

Embodiment 24. The transgenic animal of any of embodiments 21-23, wherein the pseudogenes are less than 400 nt in length.

Embodiment 25. The transgenic animal of any of embodiments 21-24, wherein the pseudogenes are 300-400 nucleotides in length.

Embodiment 26. A method comprising: (a) immunizing a transgenic animal of any prior embodiment with an antigen; and (b) obtaining from said animal an antibody that specifically binds to said antigen.

Embodiment 27. The method of embodiment 26, wherein the antibody is polyclonal.

Embodiment 28. The method of embodiment 26, wherein the antibody is monoclonal.

Embodiment 29. The method of any of embodiments 26-28, further comprising: (c) making hybridomas using B cells of said transgenic animal; and (d) screening said hybridomas to identify a hybridoma that produces an antibody that specifically binds to the antigen.

Embodiment 30. The method of any of embodiments 26-28, further comprising: (c) screening B cells without making hybridomas to identify a B cell that produces an antibody that specifically binds to the antigen.

Embodiment 31. The method of any of embodiments 26-30, further comprising using PCR to amplify at least the heavy chain variable region-encoding nucleic acid from B cells of the transgenic animal, and expressing a recombinant antibody using said amplified nucleic acid.

Embodiment 23. A polyclonal antibody produced by a transgenic animal of any of embodiments 1-25, wherein at least 50% of the antibodies in said antiserum have substantially the same light chain sequence.

Embodiment 33. A population of at least 1000 B cells produced by a transgenic animal of any of embodiments 1-25, wherein at least 50% of the B cells produce antibodies that have substantially the same light chain sequence.

Embodiment 34. A B cell isolated from an animal of any of embodiments 1-25.

Embodiment 35. A monoclonal antibody produced by an animal of any of embodiments 1-25.

EXAMPLES

The following examples are provided in order to demonstrate and further illustrate certain embodiments and aspects of the present invention and are not to be construed as limiting the scope thereof.

Example 1

Construction of CmLC1 Chickens

CmLC1 is a construct for insertion into the germline of transgenic chickens for the expression of a fixed, or unmutated, human kappa light chain in the B cell lineage. The construct is designed to insert into the chicken light chain locus and use the endogenous transcriptional regulatory elements to drive expression in B cells. The construct contains a single functional V-kappa gene, consisting of a pre-rearranged human germline VK3-15*01 gene joined to a human germline JK1*01 gene. The sequence was designed and synthesized as a pre-rearranged V region. This V region sequence is commonly found in the human-derived sequences present in the NCBI database, and is therefore equivalent to a naturally occurring sequence. Upstream of the single functional V region was placed an array of 6 pseudogenes, of identical DNA sequence to the expressed V region. All 6 pseudogenes are in reverse orientation relative to the single functional V region. They are defined as pseudogenes because they lack promoters for transcription, they lack splice donors for splicing to the downstream constant region, they do not contain translation start sites, and they do not contain signal peptide leader sequences for secretion. In gene converting species such as the chicken, these upstream pseudogenes are normally used as a source of sequence diversity with which to mutate the single functional V region by the process of gene conversion. In the case of the CmLC1 construct, attempted gene conversion by the pseudogenes would not introduce any sequence changes, rather, it would tend to revert any changes that had arisen by random somatic hypermutation in the functional V back to the germline sequence. The pseudogenes thus have a cleansing effect on the functional V, retaining the original germline sequence.

Figure 4:
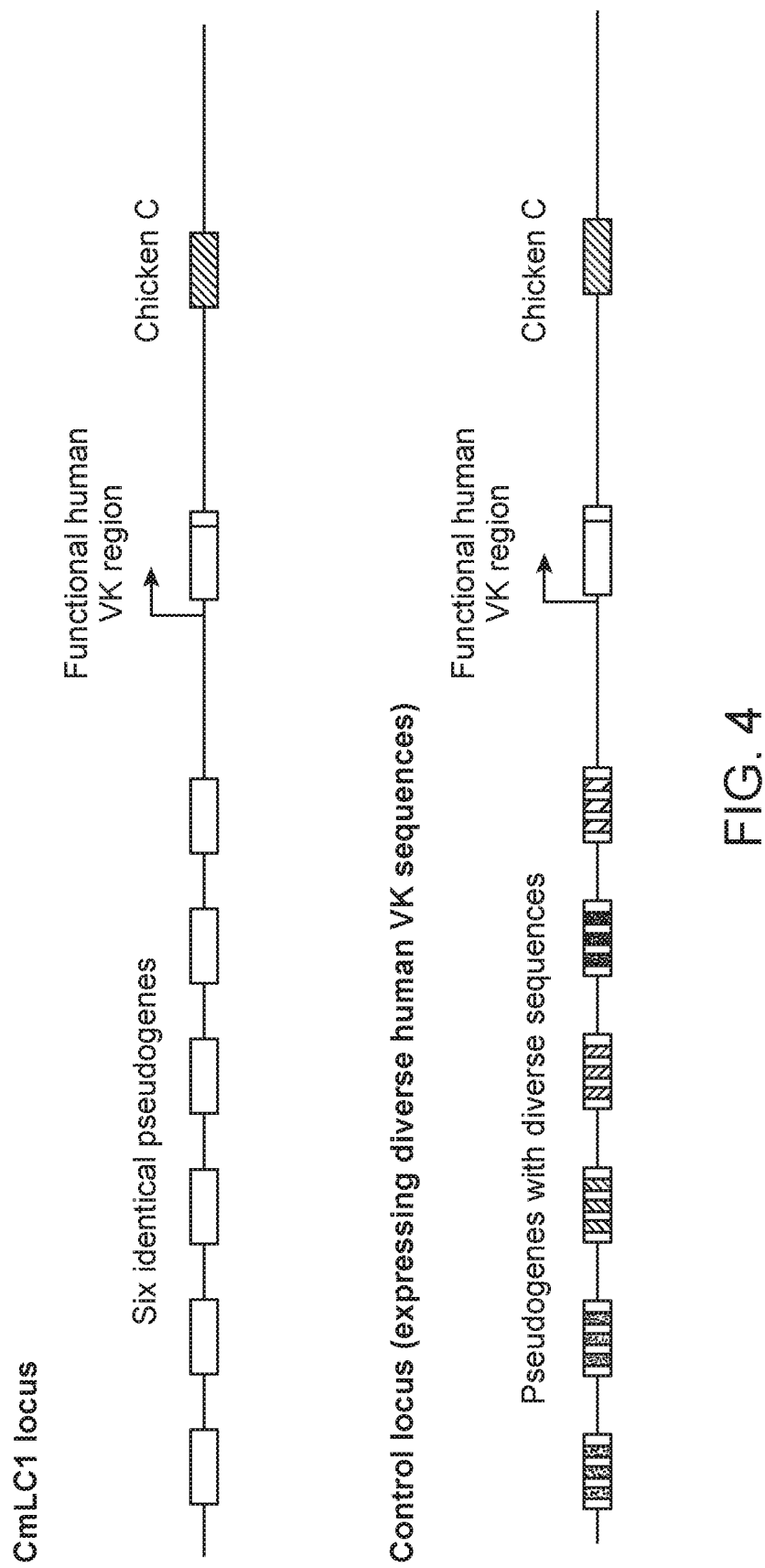
FIG. 4 illustrates the CmLC1 locus. In the CmLC1 locus, there is a single human functional variable region. Upstream of the functional VK region are 6 copies of an identical pseudogene, which are identical to the DNA sequence of the VK region in the functional gene. Also shown is a control locus that contains pseudogenes that are not identical to the functional gene.

FIG. 4 illustrates the CmLC1 locus. This locus is designed to express a chimeric light chain consisting of a human VK3-15/JK1 variable region, spliced to a chicken constant region. In the CmLC1 locus, there is a single human functional variable region. Upstream of the functional VK region are 6 copies of an identical pseudogene, which are identical to the DNA sequence of the VK region in the functional gene. These pseudogenes can participate in gene conversion to revert any mutations that may arise in the functional V back to the germline sequence.

Downstream of the V region lies the chicken light chain constant region. The CmLC light chain is thus a chimeric light chain consisting of human variable region-chicken constant region. Non-coding sequences on the construct, such as the promoter, the leader intron, the J-C intron, and the 3' UTR are all derived from the chicken light chain locus. An attB site for insertion into an attP site previously targeted to the light chain locus, using phiC31 integrase, is also included. To select for the integrase-mediated insertion, a B-actin promoter is included, which will insert upstream of a neo gene in the locus and activate its transcription, allowing for G418 selection of correct integrants. Finally, a loxP site is situated on the construct such that after insertion of the construct into the genome, Cre recombination can be used to remove the plasmid backbone and all selectable markers, leaving behind only the immunoglobulin sequences and a single loxP site and attR site.

Figure 5:
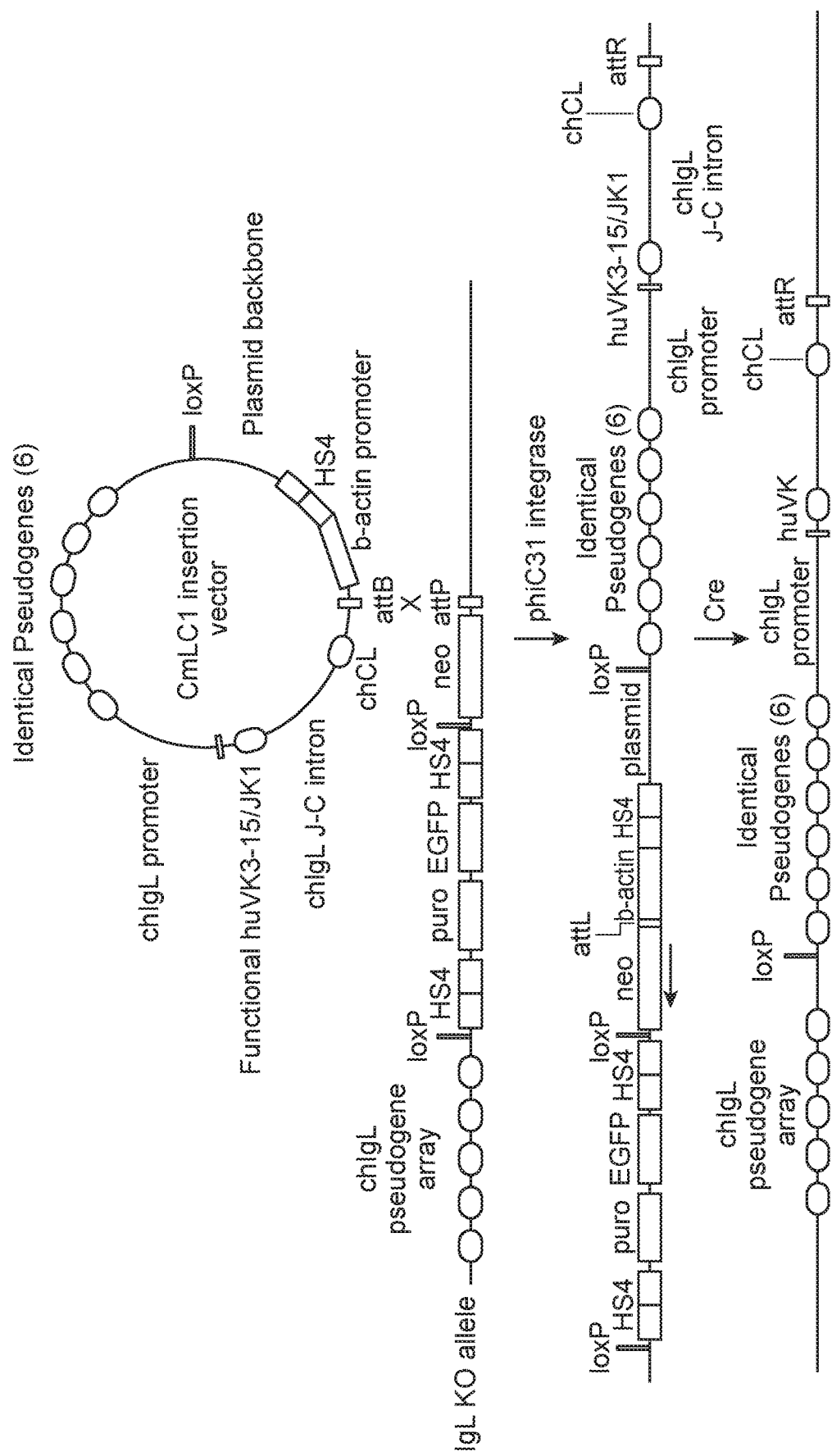
FIG. 5 schematically illustrates how the CmLC1 locus was made.
Figure 6:
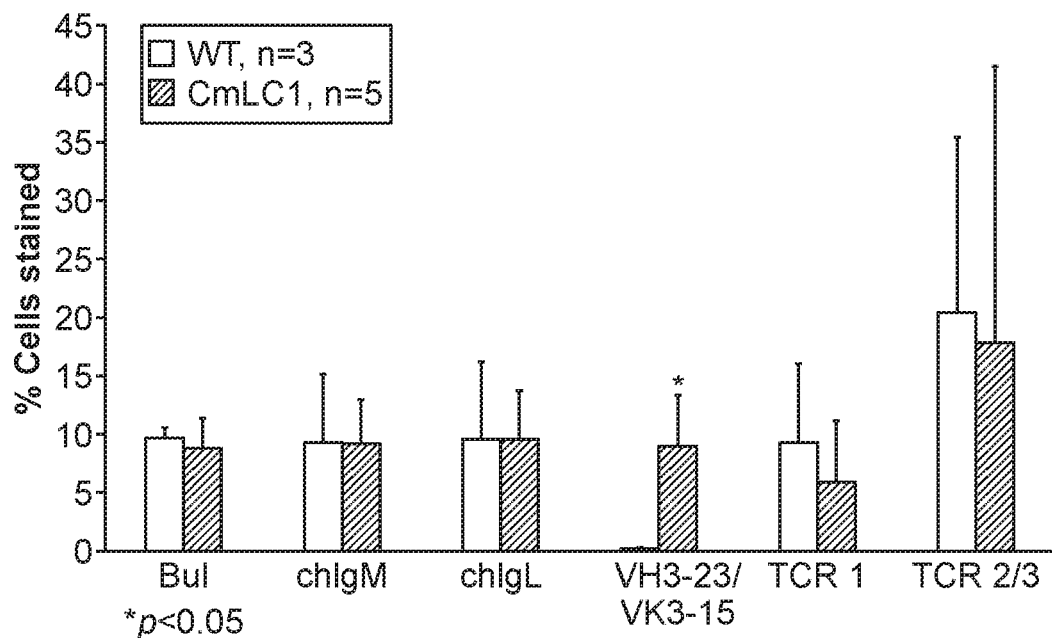
FIG. 6 is a graph showing that CmLC1/chicken VH birds have normal B cell populations in the periphery.
Figure 7:
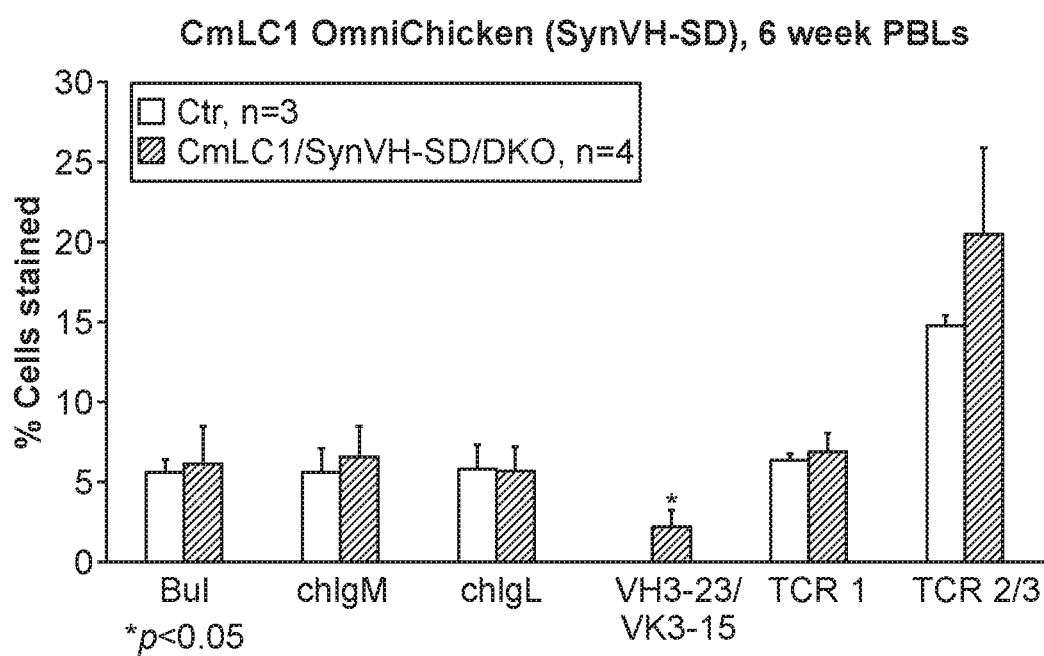
FIG. 7 is a graph showing that CmLC1/SynVH-SD birds have normal B cell populations in the periphery.

FIG. 5 illustrates how the CmLC1 locus was made. The CmLC1 insertion vector was transfected into chicken primordial germ cells carrying a knockout of the light chain locus (IgL KO allele). The light chain V-J-C region was replaced with a selectable marker cassette including a promoterless neo gene with an adjacent attP site. The attP site is recognized by phC31 integrase and is used for insertion of the CmLC1 plasmid, which is carrying an attB site and a b-actin promoter. Upon insertion, the b-actin promoter drives expression of the neo gene and provides resistant to the drug G418. In the final step, Cre recombination is used to removed the selectable markers and plasmid backbone, leaving behind a single loxP site, a single attR site, the CmLC1 functional V and pseudogenes. The chicken light chain pseudogenes remain upstream, but they were not found to introduce sequence diversity into the human functional V.

Five birds with CmLC1/IgL KO and wild type heavy chain were analyzed by flow cytometry. PBLs were prepared by Ficoll density gradient centrifugation and stained with antibodies against the chicken B cell marker Bu1, chicken IgM (heavy chain-specific), chicken IgL (constant region-specific), an antisera raised against human VK/VH, and T cell markers TCR1 and TCR2/3. All of the B cell populations looked normal as compared to 3 wild type control birds. The anti-human VK/VH antibodies only stained the CmLC1 birds, as expected. This data is shown in FIG. 5. This data shows that CmLC1/chicken VH birds have normal B cell populations (i.e., similar to wild type control birds) in the periphery.

PBLs from four birds with the genotype CmLC1/SynVH-SD/IgL KO/IgH KO were analyzed by flow cytometry. These birds express chimeric antibodies consisting of human VK and human VH. PBLs were prepared by Ficoll density gradient centrifugation and stained with antibodies against the chicken B cell marker Bu1, chicken IgM (heavy chain-specific), chicken IgL (constant region-specific), an antiserum raised against human VK/VH, and T cell markers TCR1 and TCR2/3. All of the B cell populations looked normal as compared to 3 wild type control birds. The anti-human VK/VH antibodies only stained the PBLs from CmLC1 birds, as expected. These chickens also have normal B cell populations in the periphery.

In the next set of experiments, a small cohort of each genotype was immunized with human progranulin. Antigen-specific clones identified with the GEM assay (see U.S. Pat. No. 8,030,095). Epitope binning and kinetics analysis was performed and the antibodies were evaluated for cross-reactivity. The clones were sequenced and sequence diversity of the CmLC1 birds was compared to the control birds that do not have pseudogenes that are identical.

Figure 8:
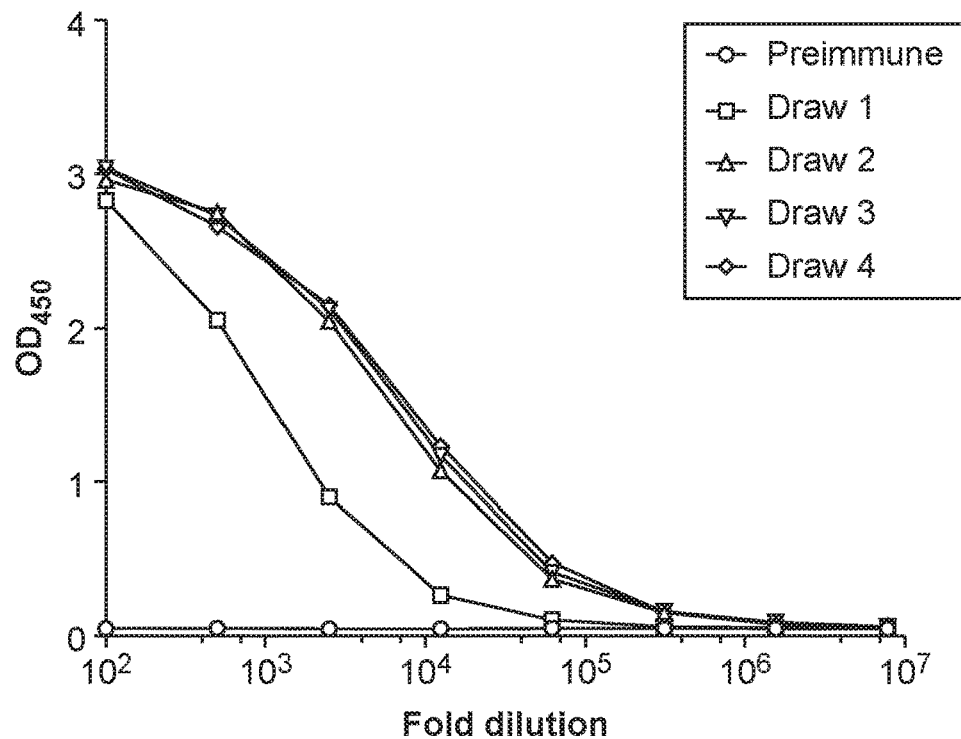
FIG. 8 shows the progranulin-specific titers in CmLC1-expressing birds. This data shows that CmLC1-expressing birds produce robust antibody titers against human progranulin.
Figure 8:
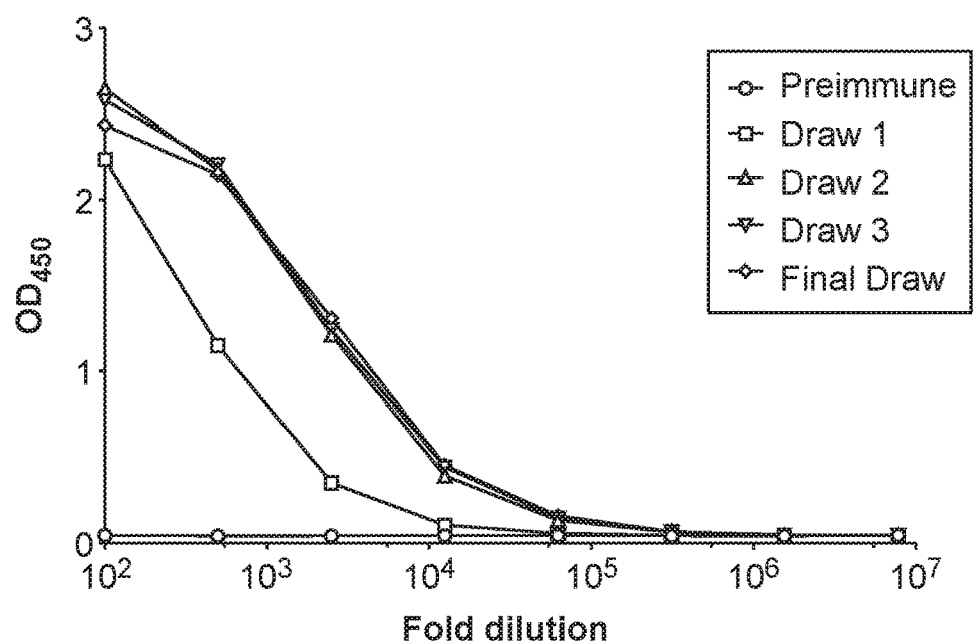

Progranulin-specific titer was monitored over time in CmLC1-expressing birds. This data is shown in FIG. 8. Strong titers were observed, similar to those obtained in controls (with diversifying light chains) and wild type birds. Top panel, CmLC1-bird with wild type heavy chain. Bottom panel, chickens with human heavy chain V region, as shown in FIG. 4.

Figure 9:
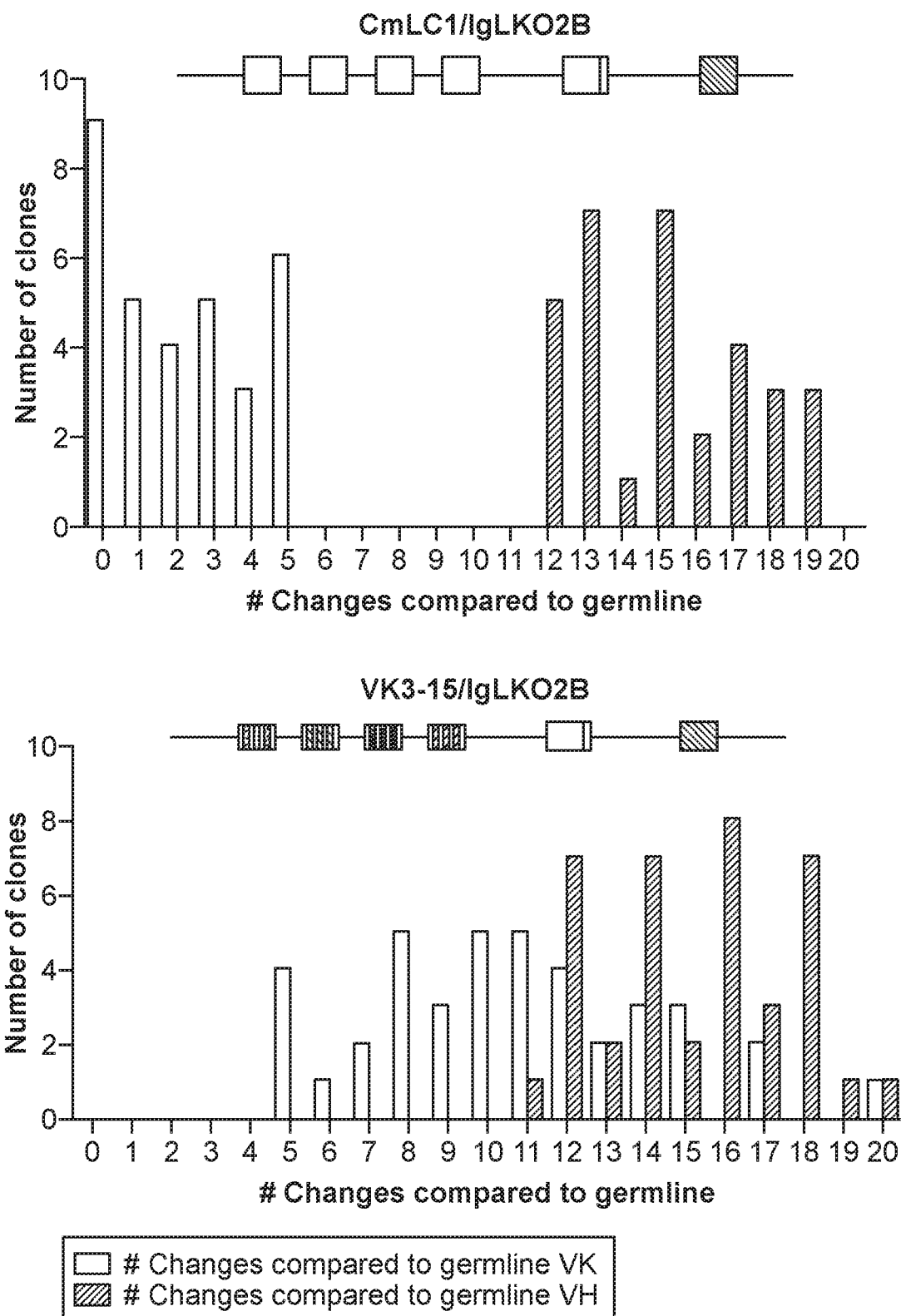
FIG. 9 shows the analysis of sequences of the VK and VH regions from a group of 32 monoclonal antibodies obtained from CmLC1 (top panel) compared to antibodies obtained in a bird with a diversifying human light chain (bottom panel). This shows that antigen-specific clones have little amino acid diversity in the light chain.

Sequences of the VK and VH regions from a group of 32 monoclonal antibodies obtained from CmLC1 (top panel of FIG. 9) were compared to antibodies obtained in a bird with a diversifying human light chain (bottom panel of FIG. 9). For each antibody sequence, the total number of changes per variable region sequence compared to the germline sequence was counted. VK is in blue, VH is in red. The results show that for CmLC1-derived antibodies, there is a clear reduction in the number of changes in the light chain, compared to a human transgene that undergoes normal affinity maturation. For the heavy chain, both CmLC1 and the normal VK3-15 bird contained many changes per sequence. This data shows that antigen-specific clones from CmLC1 birds have little amino acid diversity in the light chain.

Figure 10:
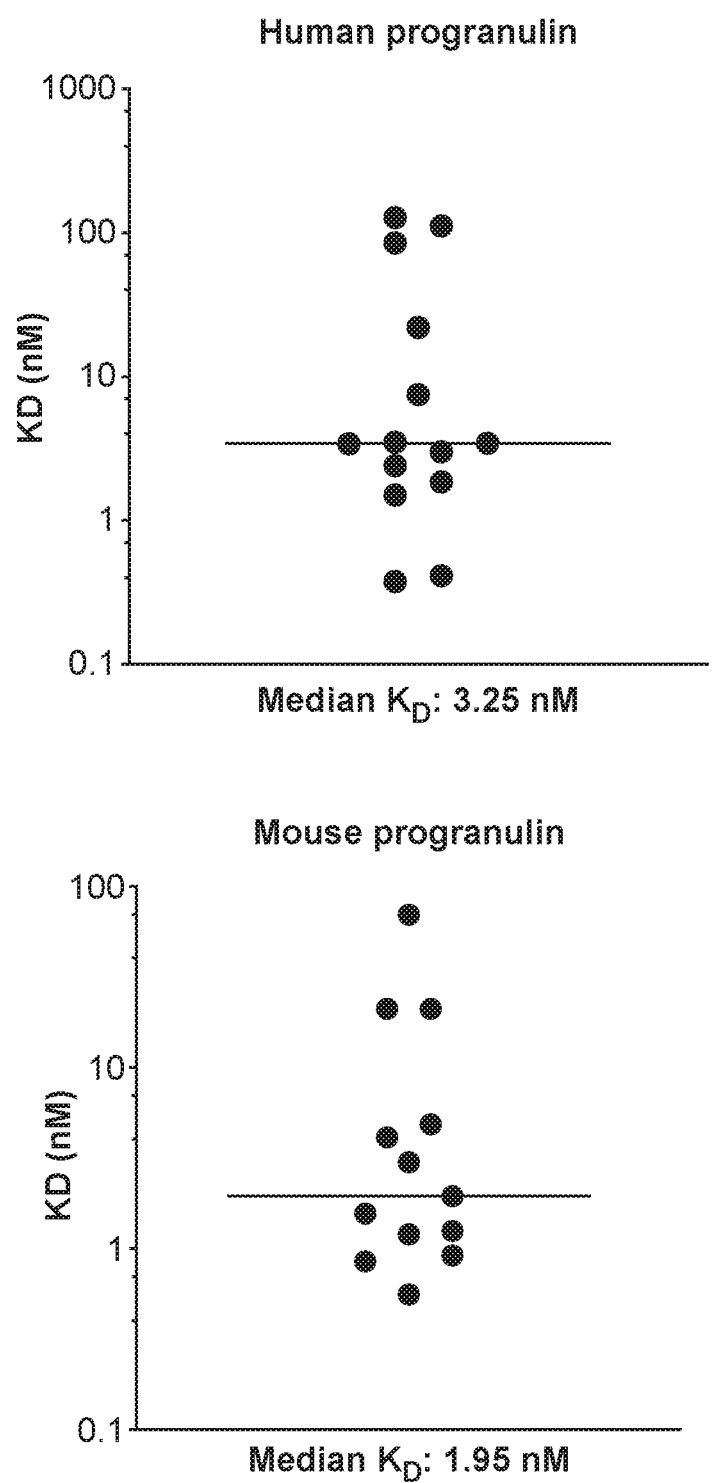
FIG. 10 shows results from surface plasmon resonance analysis. This data shows that some CmLC1 clones bind to both human and mouse progranulins with subnanomolar $K_D$.

A cohort of CmLC1 antibodies was analyzed by surface plasmon resonance in order to determine binding affinities to the antigen human progranulin (top) and mouse progranulin (bottom). See FIG. 10. Many of the antibodies are cross-reactive to the mouse protein, and the binding affinities to the mouse are shown (bottom). Many of the antibodies showed very high affinity to the antigen. The median binding affinity is 3.25 nM, and some antibodies had subnanomolar affinities (<1 nM).

Figure 11:
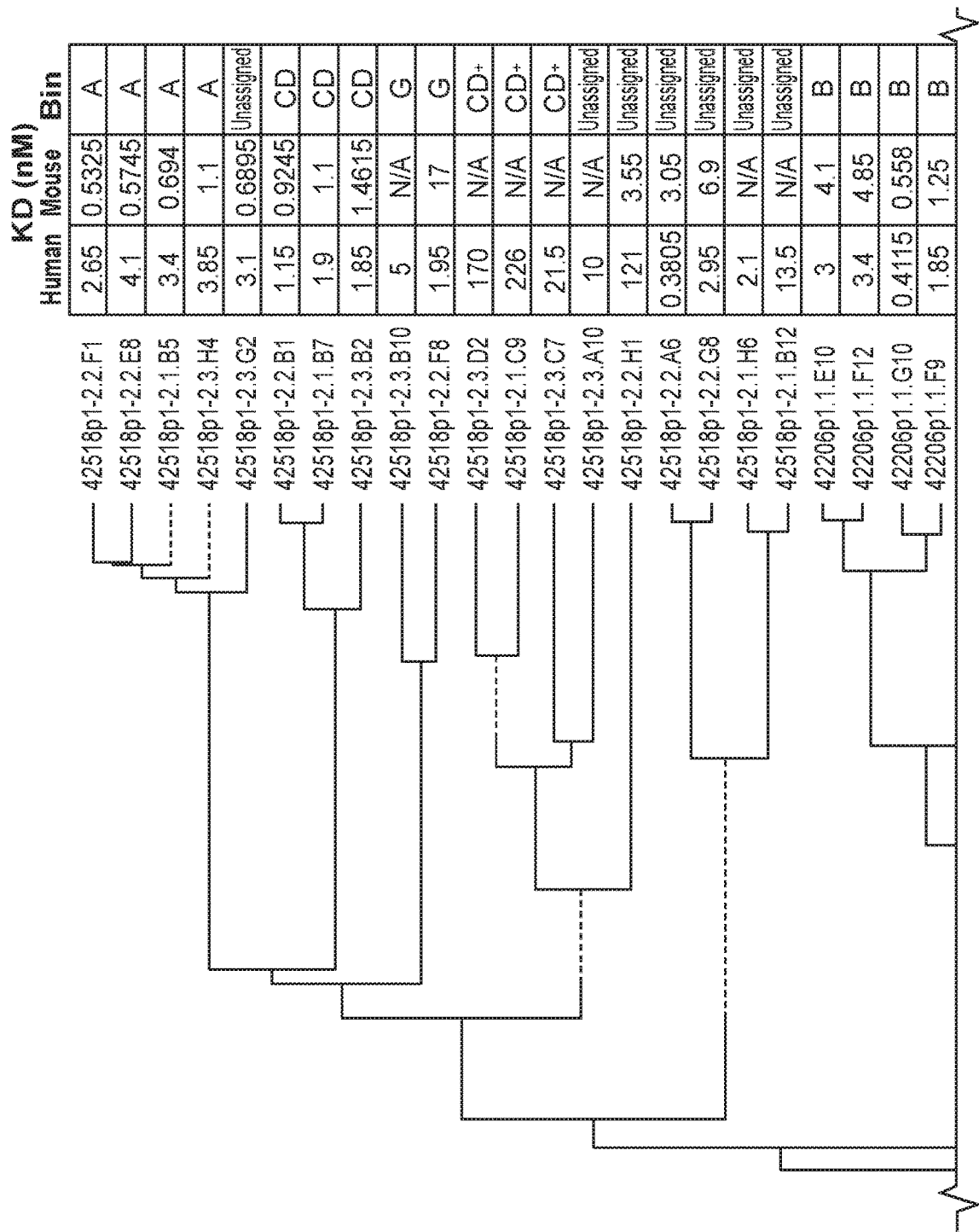
FIG. 11 shows the cross-blocking relationships and epitope binning analysis of CmLC1 birds. This data shows that CmLC1 antibodies have a broad epitope coverage.

The cohort of CmLC1-derived antibodies was also analyzed by high-throughput array SPR in order to determine cross-blocking relationships and epitope binning. This data is shown in FIG. 11. The epitope bins on progranulin were defined by a set of antibody standards of known binding. The epitope bins are shown in the column to the right. The binding affinities to the human and mouse progranulin are shown in the other two columns. The sequence dendrogram is showing how the antibodies are related, and in general, sequences that correspond to an epitope bin are related to each other.

The experiments described above show that:

CmLC1 chickens retain the antigen recognition capabilities of the control chickens as well as wild type chickens;

CmLC1 antibodies retain high specificity and binding affinity found in the control chickens; and CmLC1 technology can be used to make common light chain antibodies, i.e., antibodies in which the VK has an essentially germline sequence and the diversity entirely on the VH domain.

Example 2

Construction of the CmLC4 Locus

CmLC4 is a construct for insertion into the germline of transgenic chickens for the expression of a fixed, or unmutated, human kappa light chain in the B cell lineage. The construct is designed to insert into the chicken light chain locus and use the endogenous transcriptional regulatory elements to drive expression in B cells. The construct contains four copies of a functional light chain gene, consisting of a pre-rearranged human germline VK3-15*01 gene joined to a human germline JK1*01 gene and a chicken constant region gene. Each copy of the functional light chain gene (VJC) contains its own promoter. The light chain 3' enhancer lies downstream and was not quadruplicated. The light chain gene was designed and synthesized as a pre-rearranged human V region, fused in-frame to the chicken constant region. This V region sequence is commonly found in the human-derived sequences present in the NCBI database, and is therefore equivalent to a naturally occurring variable region. Upstream of the four functional V regions was placed an array of 6 pseudogenes, of identical DNA sequence to the functional V regions. All 6 pseudogenes are in reverse orientation relative to the four functional light chains. They are defined as pseudogenes because they lack promoters for transcription, they lack splice donors for splicing to the downstream constant region, they do not contain translation start sites, and they do not contain signal peptide leader sequences for secretion. In gene converting species such as the chicken, these upstream pseudogenes are normally used as a source of sequence diversity with which to mutate the functional V region by the process of gene conversion. In the case of the CmLC4 construct, gene conversion by the pseudogenes would not introduce any sequence changes, rather, it would tend to revert any changes that had arisen by random somatic hypermutation in the functional V back to the germline sequence. The pseudogenes thus have a cleansing effect on the functional V, returning the sequence to the original germline sequence. In addition, we provided four copies of the functional V in order to dilute out any mutations that might arise in any one of the copies. If a mutation were to arise in one of the copies, the resulting light chain protein would contribute only ¼ of the total light chain protein on the cell surface. Any single mutation could thus only provide a small boost to antigen binding. During affinity maturation and clonal selection in the germinal center, beneficial mutations would not be positively selected efficiently, because any one mutation will only contribute part of the overall light chain pool on the cell surface.

The CmLC4 light chain is a chimeric light chain consisting of human variable region-chicken constant region. Non-coding sequences on the construct, such as the four promoters, the leader intron, and the 3' UTRs are all derived from the chicken light chain locus. An attB site for insertion into an attP site previously targeted to the light chain locus, using phiC31 integrase, is also included. To select for the integrase-mediated insertion, a B-actin promoter is included, which will insert upstream of a neo gene in the locus and activate its transcription, allowing for G418 selection of correct integrants. Finally, a loxP site is situated on the construct such that after insertion of the construct into the genome, Cre recombination can be used to remove the plasmid backbone and all selectable markers, leaving behind only the immunoglobulin sequences and a single loxP site and attR site.

Figure 12:
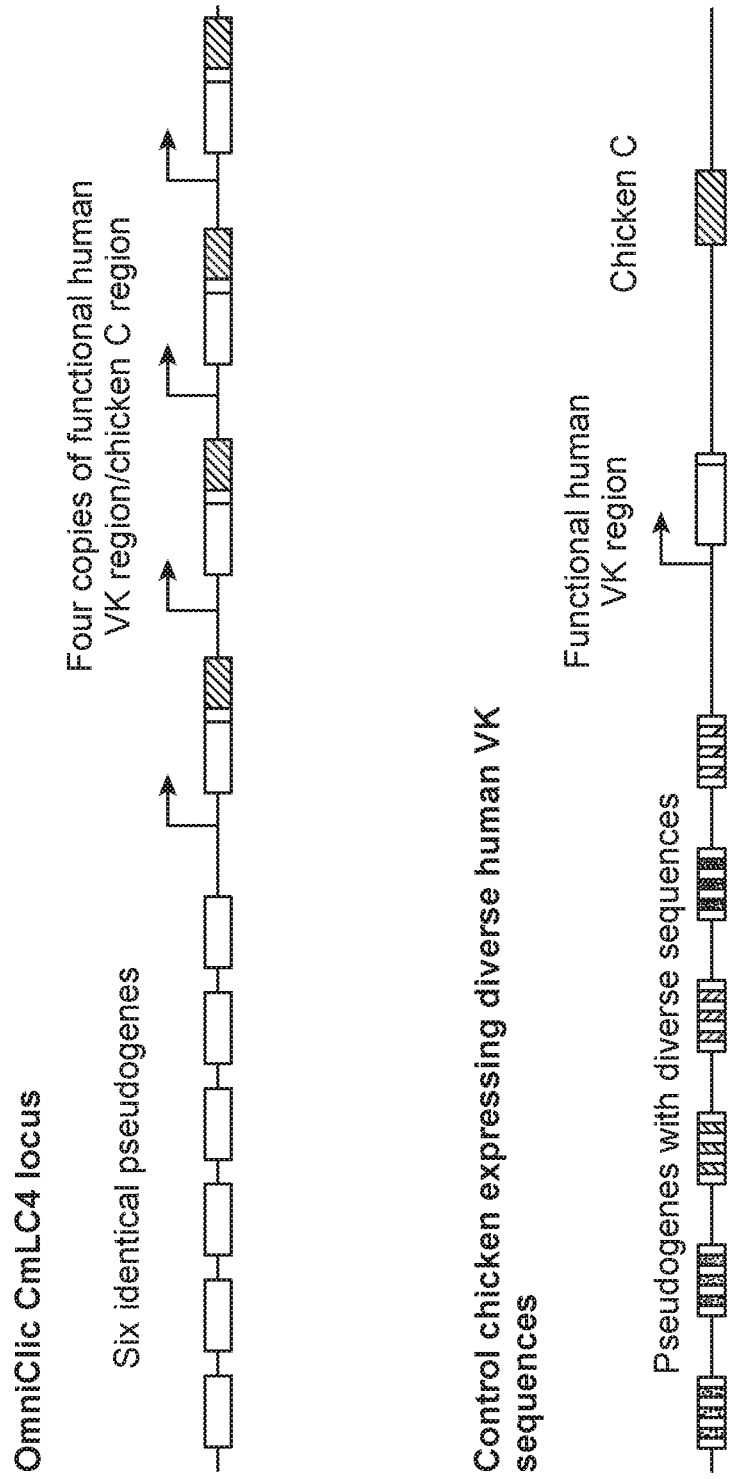
FIG. 12 illustrates the CmLC4 locus. In the CmLC4 locus there are four copies of an identical gene, each with its own promoter (shown by the arrows), encoding human VK-chicken CL light chain.

FIG. 12 illustrates the CmLC4 locus. This locus is designed to express a chimeric light chain consisting of a human VK3-15/JK1 variable region, joined to a chicken constant region. In the CmLC4 locus, there are four copies of an identical gene, each with its own promoter (shown by the arrows), encoding human VK-chicken CL light chain. These four copies are the functional light chain genes. Upstream of the functional light chains are 6 copies of an identical pseudogene, which are identical to the DNA sequence of the VK regions in the functional genes (as used in the CmLC1 locus described above). These pseudogenes can participate in gene conversion to revert mutations that may arise in the functional genes back to the germline sequence.

Figure 13:
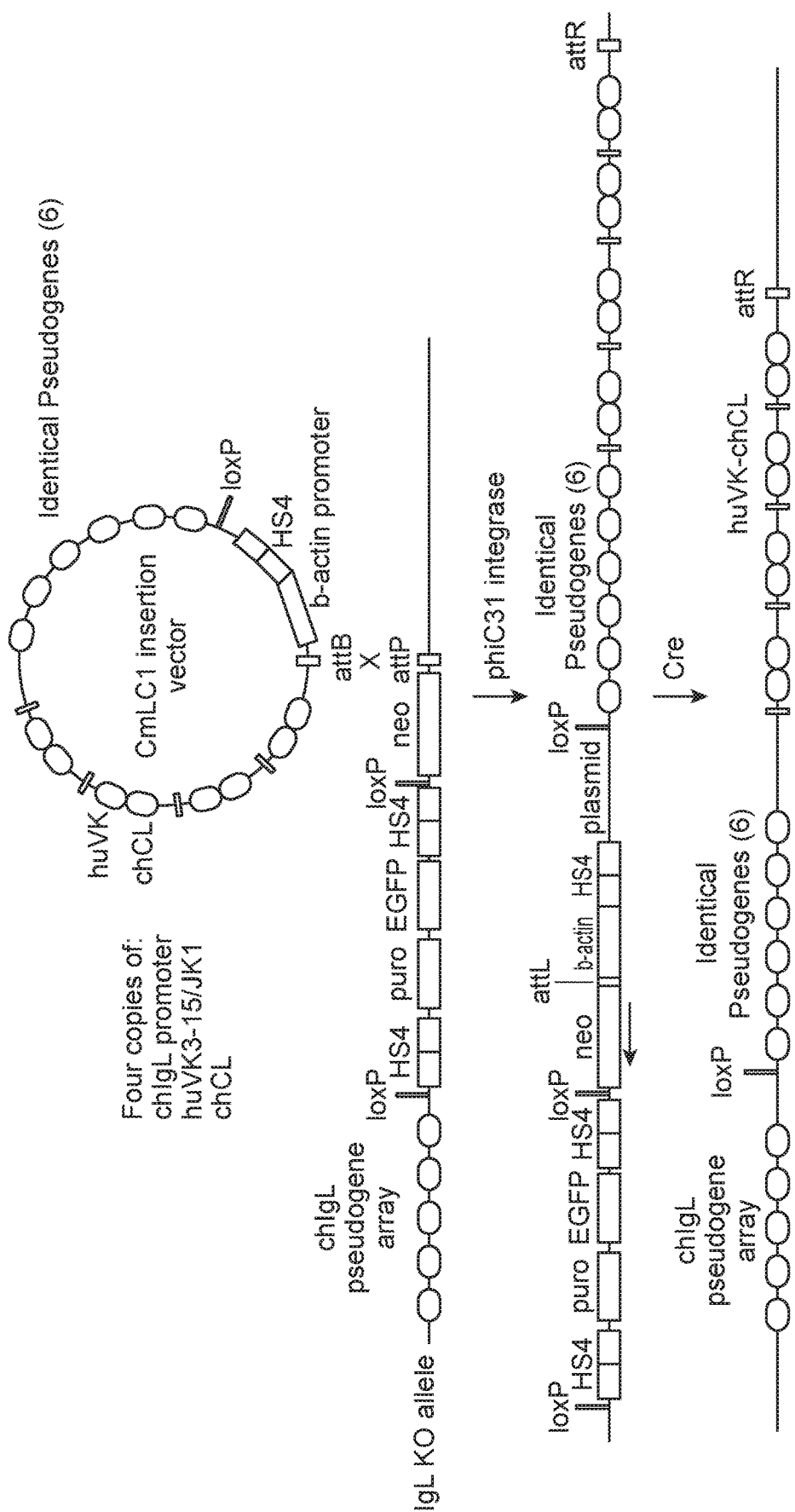
FIG. 13 illustrates how the CmLC4 locus was made.

FIG. 13 illustrates how the CmLC4 locus was made. As shown, the CmLC1 vector was transfected into chicken primordial germ cells carrying a knockout of the light chain locus (insertionIgL KO allele). The light chain V-J-C region was replaced with a selectable marker cassette including a promoterless neo gene with an adjacent attP site. The attP site is recognized by phC31 integrase and is used for insertion of the CmLC1 plasmid, which is carrying an attB site and a b-actin promoter. Upon insertion, the b-actin promoter drives expression of the neo gene and provides resistant to the drug G418. In the final step, Cre recombination is used to removed the selectable markers and plasmid backbone.

Figure 14:
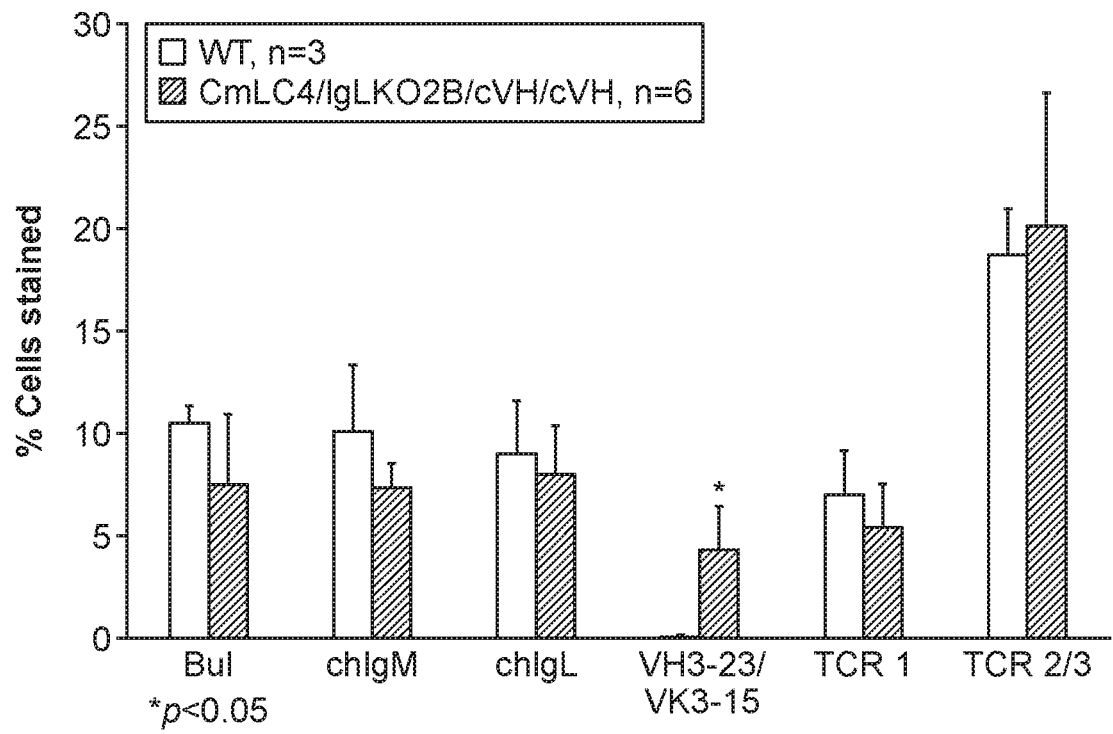
FIG. 14 is a graph showing that CmLC4/chicken VH birds have normal B cell populations in the periphery.

PBL from six birds with CmLC4/IgL KO and wild type heavy chain were analyzed by flow cytometry (see FIG. 14). PBL were prepared by Ficoll density gradient centrifugation and stained with antibodies against the chicken B cell marker Bu1, chicken IgM (heavy chain-specific), chicken IgL (constant region-specific), an antisera raised against human VK/VH, and T cell markers TCR1 and TCR2/3. All of the B cell populations looked normal as compared to 3 wild type control birds. The anti-human VK/VH antibodies only stained the CmLC4 birds, as expected. This data shows that CmLC4/chicken VH birds have normal B cell populations in the periphery.

Figure 15:
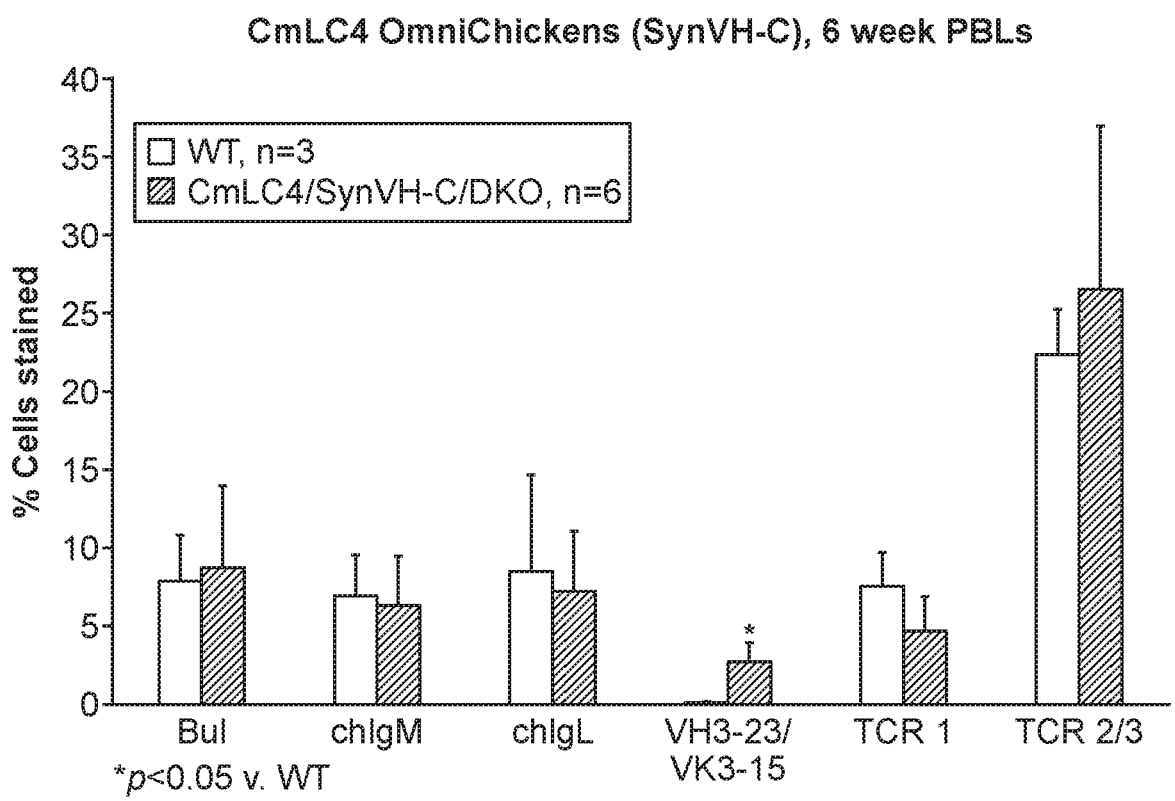
FIG. 15 is a graph showing that CmLC4/SynVH-C birds have normal B cell populations in the periphery.

Six birds with the genotype CmLC4/SynVH-C/IgL KO/IgH KO were analyzed by flow cytometry (see FIG. 15). These birds express chimeric antibodies consisting of human VK and human VH. PBL were prepared by Ficoll density gradient centrifugation and stained with antibodies against the chicken B cell marker Bu1, chicken IgM (heavy chain-specific), chicken IgL (constant region-specific), an antiserum raised against human VK/VH, and T cell markers TCR1 and TCR2/3. All of the B cell populations looked normal as compared to 3 wild type control birds. The anti-human VK/VH antibodies only stained the CmLC4 birds, as expected. This data also shows that CmLC4 birds have normal B cell populations in the periphery.

In the next set of experiments, a small cohort of each genotype was immunized with human progranulin. Antigen-specific clones identified with the GEM assay (see U.S. Pat. No. 8,030,095). Epitope binning and kinetics analysis was performed and the antibodies were evaluated for cross-reactivity. The clones were sequenced and sequence diversity of the CmLC1 birds was compared to the control birds.

Figure 16:
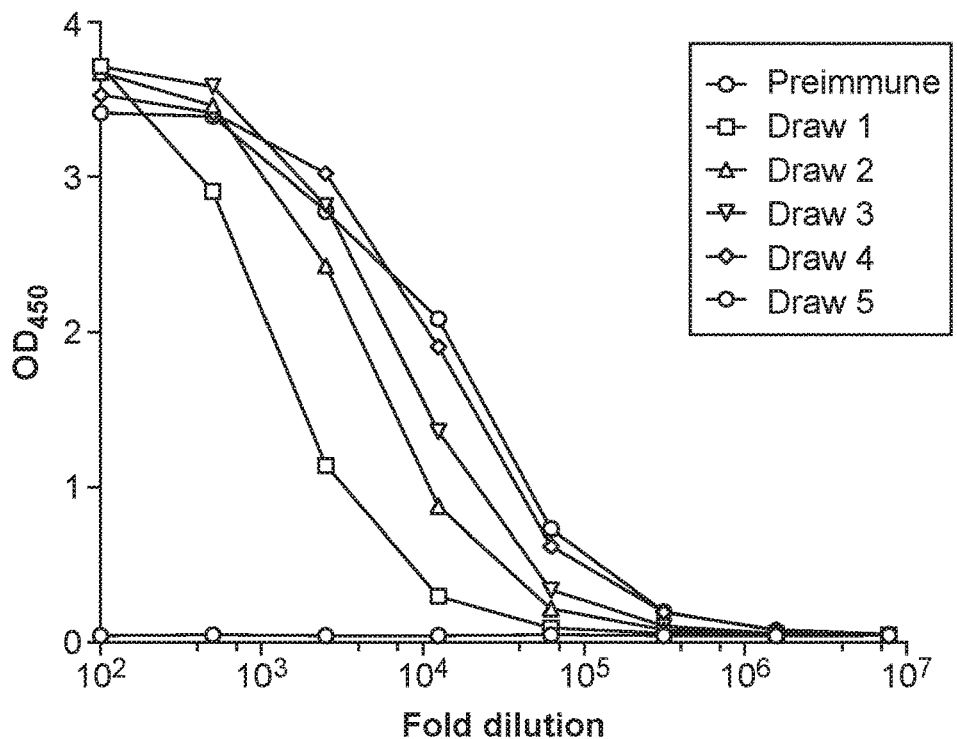
FIG. 16 shows the progranulin-specific titers in CmLC4-expressing birds. This data shows that CmLC4-expressing birds produce robust antibody titers against human progranulin.
Figure 16:
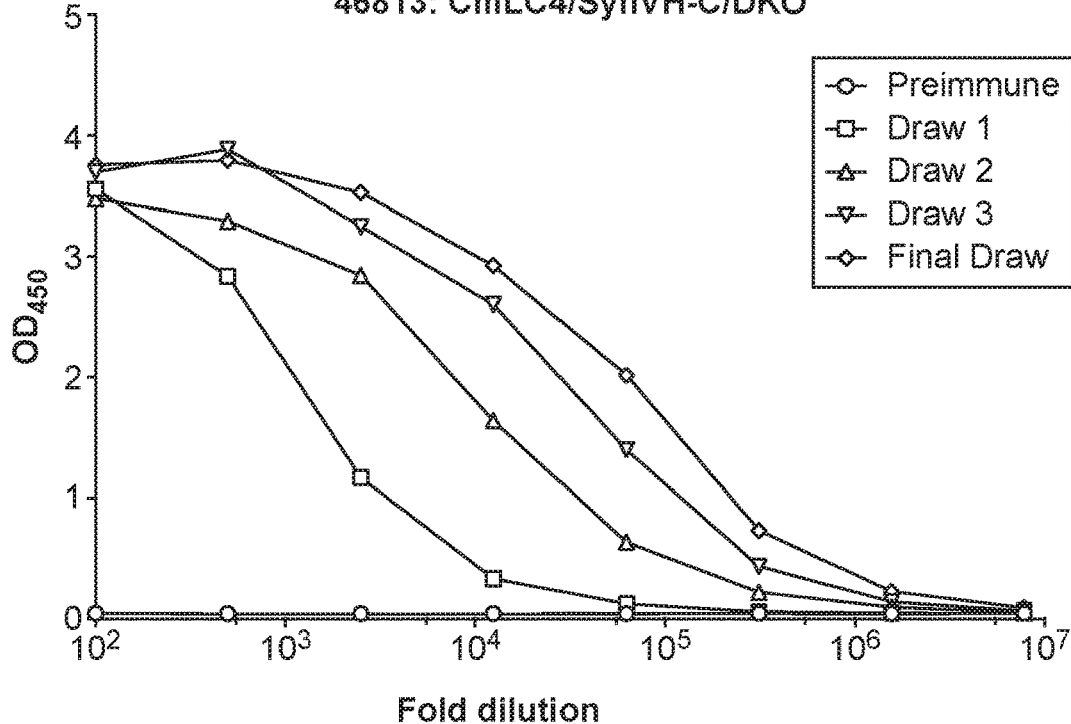

Progranulin-specific titer was monitored over time in CmLC4-expressing birds. These results are shown in FIG. 16. Strong titers were observed, similar to those obtained in the controls (with diversifying light chains) and wild type birds. Top panel, CmLC4-bird with wild type heavy chain. Bottom panel, OmniClic (CmLC4) with human heavy chain V region.

Figure 17:
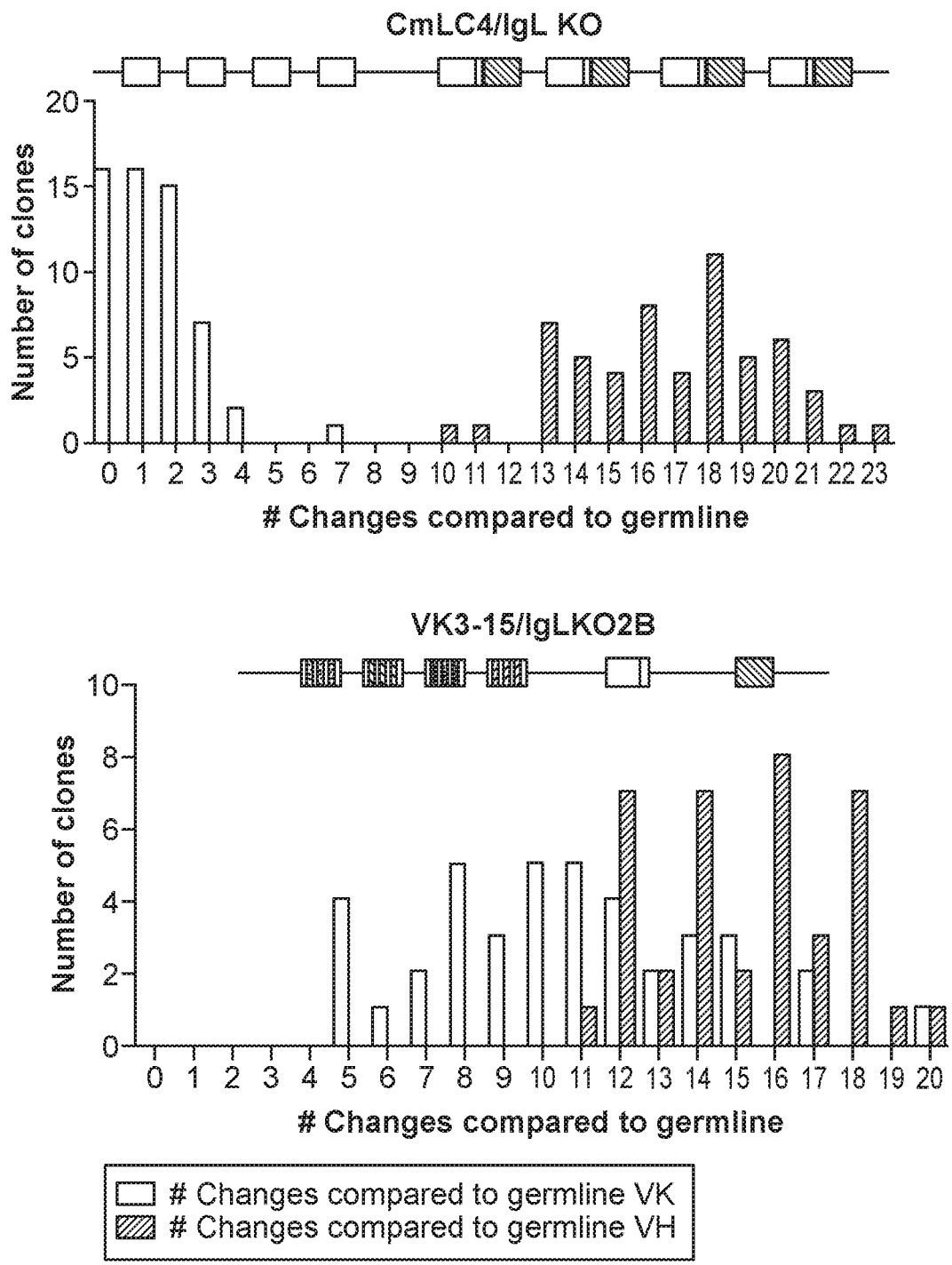
FIG. 17 shows the analysis of sequences of the VK and VH regions from a group of 56 monoclonal antibodies obtained from CmLC4 (top panel) compared to antibodies obtained in a bird with a diversifying human light chain (bottom panel). This shows that antibodies obtained from CmLC4 birds have reduced amino acid diversity in the light chain compared to birds with a diversifying light chain.

Sequences of the VK and VH regions from a group of 56 monoclonal antibodies obtained from CmLC4 (top panel of FIG. 17) were compared to antibodies obtained in a bird with a diversifying human light chain (bottom panel of FIG. 17). For each antibody sequence, the total number of changes per variable region compared to the germline sequence was counted. VK is in blue, VH is in red. The results show that for CmLC4-derived antibodies, there is a clear reduction in the number of changes in the light chain, compared to a human transgene that undergoes normal affinity maturation. For the heavy chain, both CmLC4 and the normal VK3-15 bird contained many changes per sequence.

Figure 18:
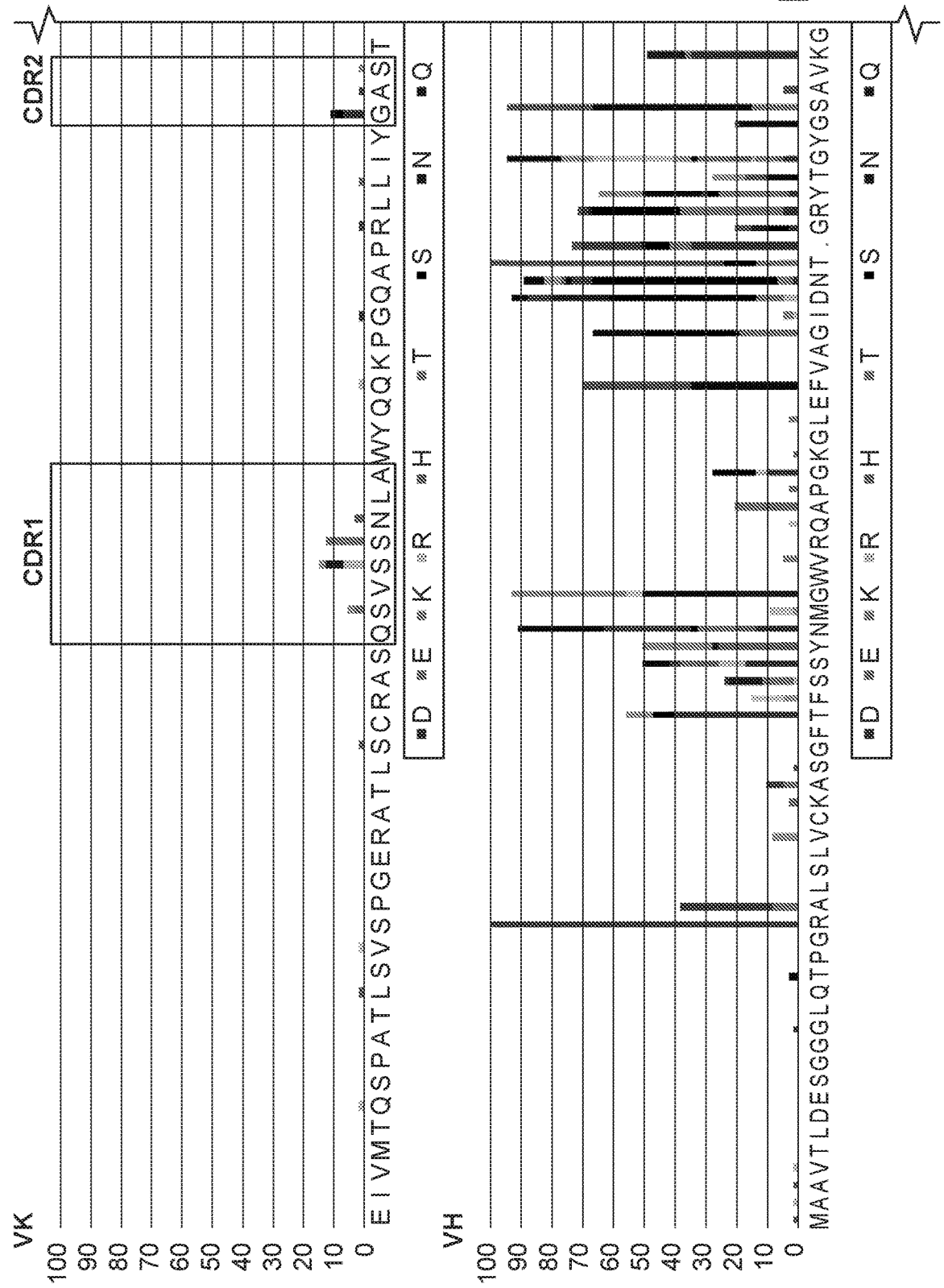
FIG. 18 shows the amino acid diversity of a set of 56 monoclonal antibodies from a CmLC4 bird. SEQ ID NOS: 1 and 2.
Figure 18:
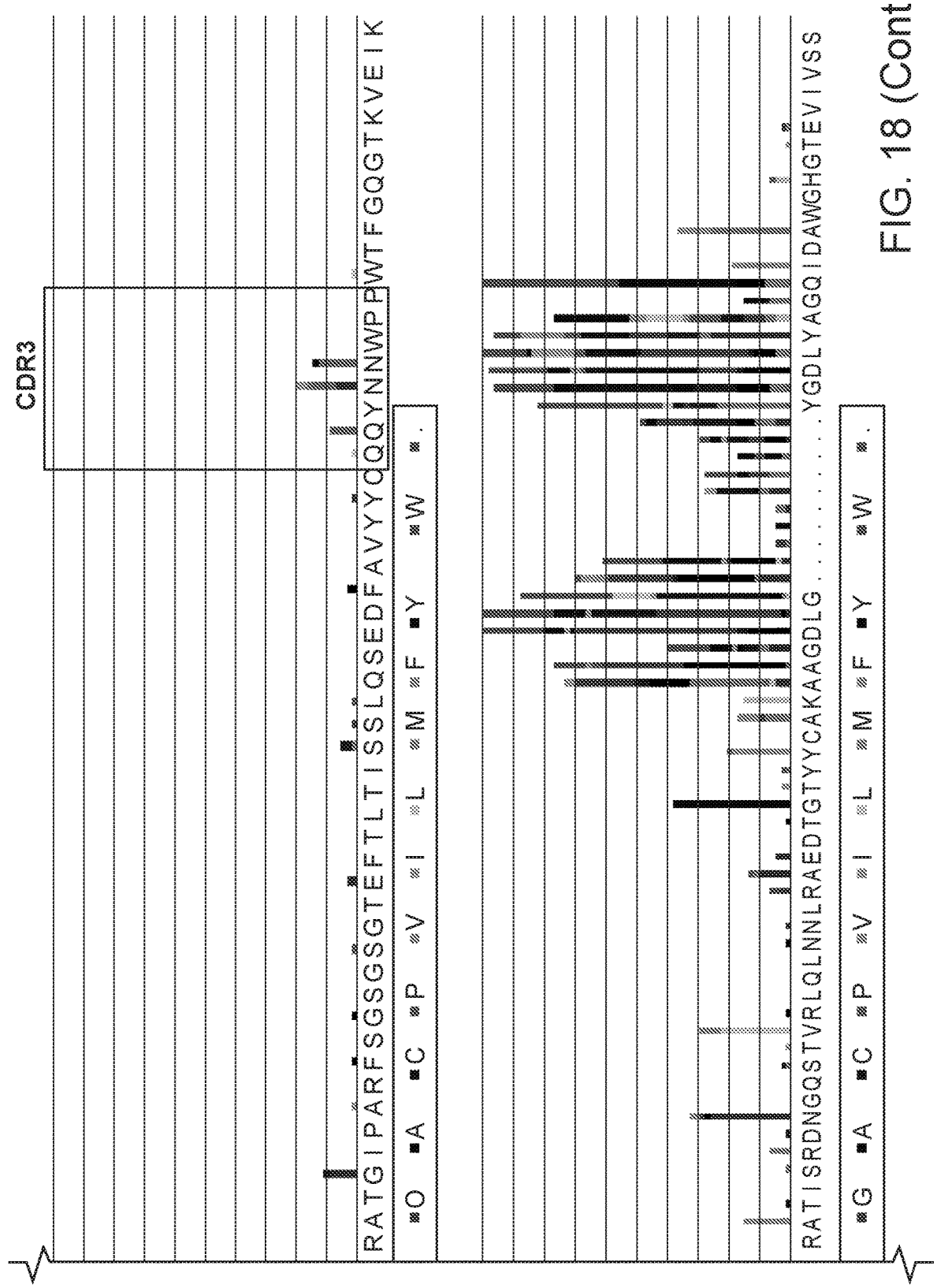

FIG. 18 shows the amino acid diversity among a set of 56 monoclonal antibodies made by CmLC4 birds. At each position in the light chain variable region (top) or heavy chain variable region (bottom), residues that differ from the germline sequence are counted. The height of the bars indicates the % of sequences that contain changes in each position. The colors indicate the amino acids found. This data shows that in CmLC4 birds, diversity is focused on the heavy chain.

Figure 19:
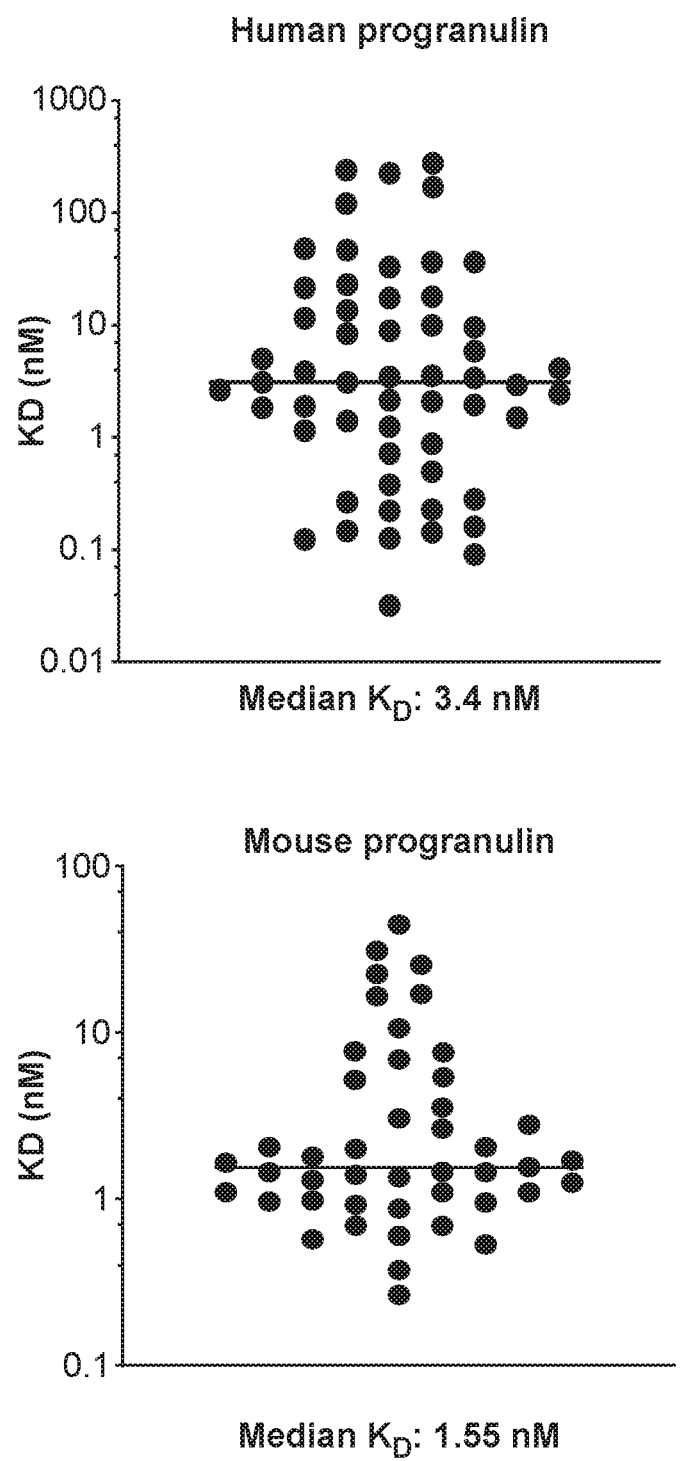
FIG. 19 shows results from surface plasmon resonance analysis. This data shows that some CmLC4 clones bind to both human and mouse progranulins with subnanomolar $K_D$.

Surface plasmon resonance on the cohort of 56 antibodies was used to determine binding affinities to the antigen human progranulin (FIG. 19, top panel) and mouse progranulin (FIG. 19, bottom panel). Many of the antibodies are cross-reactive to the mouse protein, and the binding affinities to the mouse are shown at right. Many of the antibodies showed very high affinity to the antigen. The median binding affinity is 3.4 nM, and many antibodies had subnanomolar affinities (<1 nM).

Figure 20:
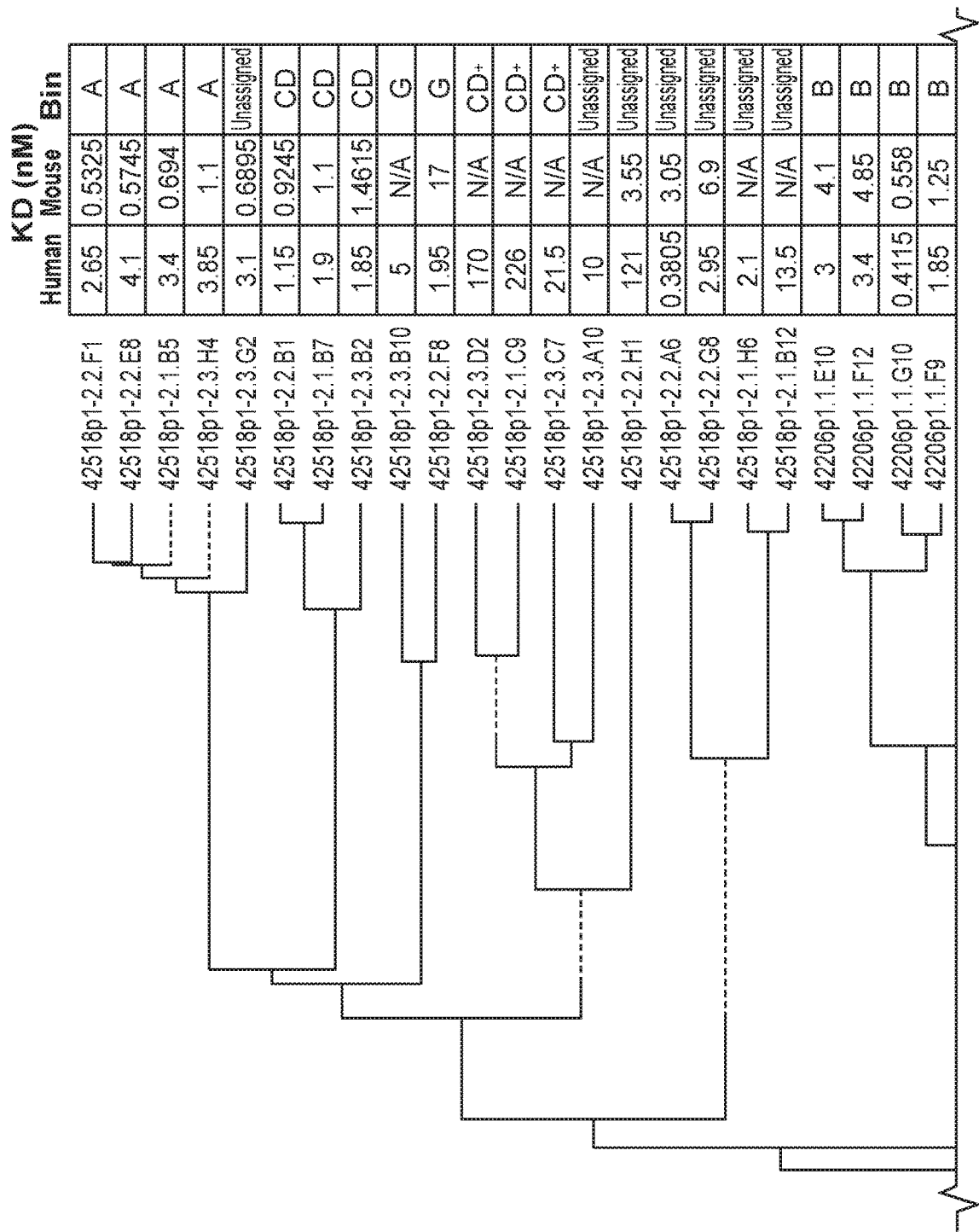
FIG. 20 shows the cross-blocking relationships and epitope binning analysis of CmLC4 birds. This data shows that CmLC4 antibodies have a broad epitope coverage.

The cohort of 56 antibodies was analyzed by high-throughput array SPR in order to determine cross-blocking relationships and epitope binning. This is shown in FIG. 20. The epitope bins on progranulin were defined by a set of antibody standards of known binding. The epitope bins are shown in the column to the right. The binding affinities to the human and mouse progranulin are shown in the other two columns. The sequence dendrogram shows how the antibodies are related, and in general, sequences that correspond to an epitope bin are related to each other.

The experiments described above show that:
CmLC4 chickens retain the antigen recognition capabilities of controls and wild type chickens;
CmLC4 antibodies retain high specificity and binding affinity found in controls; and
CmLC4 technology can be used to make common light chain antibodies, i.e., antibodies in which the VK has an essentially germline sequence and the diversity entirely on the VH domain.

What is claimed is:

1. A transgenic animal that uses gene conversion for antibody diversification, comprising a genome comprising an endogenous immunoglobulin light chain locus comprising:
    (a) a functional immunoglobulin light chain gene comprising a nucleic acid encoding a light chain variable region; and
    (b) a plurality of pseudogenes that are operably linked to said functional immunoglobulin light chain gene and that donate, by gene conversion, nucleotide sequence to the nucleic acid encoding a light chain variable region,
    wherein the pseudogenes are upstream or downstream of the functional immunoglobulin light chain gene,
    wherein each of the pseudogenes is at least 200 nucleotides in length, and
    each pseudogene in its entirety encodes the same amino acid sequence as a corresponding region in the light chain variable region of the functional immunoglobulin light chain gene of (a).

2. The transgenic animal of claim 1, wherein the pseudogenes contain a nucleotide sequence that is identical to at least part of the nucleic acid encoding a light chain variable region.

3. The transgenic animal of claim 1, wherein the transgenic animal is a chicken.

4. The transgenic animal of claim 1, wherein the nucleic acid encoding the light chain variable region of (a) comprises a variable (V) segment and a joining (J) segment.

5. The transgenic animal of claim 4, wherein the light chain variable region of (a) is encoded by a human germline light chain V segment and a human germline light chain J segment.

6. The transgenic animal of claim 5, wherein the V segment of the light chain variable region of (a) is encoded by a germline light chain kappa V segment.

7. The transgenic animal of claim 5, wherein the V segment of the light chain variable region of (a) is encoded by a germline light chain lambda V segment.

8. The transgenic animal of claim 4, wherein the pseudogenes encode at least part of the same amino acid sequence as the V segment.

9. The transgenic animal of claim 4, wherein the pseudogenes encode at least part of the same amino acid sequence as the V and J segments.

10. The transgenic animal of claim 1, wherein the light chain variable region is from a human monoclonal antibody.

11. The transgenic animal of claim 1, wherein the pseudogenes are less than 400 nt in length.

12. The transgenic animal of claim 1, wherein each of the pseudogenes is 300-400 nucleotides in length.

13. The transgenic animal of claim 1, wherein there are up to 30 of said pseudogenes.

14. A method comprising:
   (a) immunizing a transgenic animal of claim 1 with an antigen; and
   (b) obtaining from said animal an antibody that specifically binds to said antigen.

15. The method of claim 14, wherein the antibody is monoclonal.

16. The method of claim 14, further comprising:
   (c) making hybridomas using B cells of said transgenic animal; and
   (d) screening said hybridomas to identify a hybridoma that produces an antibody that specifically binds to the antigen.

17. The method of claim 14, further comprising:
   (c) screening B cells without making hybridomas to identify a B cell that produces an antibody that specifically binds to the antigen.

18. A population of at least 1000 B cells produced by a transgenic animal of claim 1, wherein at least 50% of the B cells produce antibodies that have the same light chain sequence, with the exception of up to five amino acid substitutions.

19. A B cell isolated from an animal of claim 1.

* * * * *

SEQUENCE LISTING

<160> NUMBER OF SEQ ID NOS: 2

<210> SEQ ID NO 1
<211> LENGTH: 108

```
<212> TYPE: PRT
<213> ORGANISM: Artificial sequence
<220> FEATURE:
<223> OTHER INFORMATION: synthetic sequence

<400> SEQUENCE: 1

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys
                100                 105

<210> SEQ ID NO 2
<211> LENGTH: 128
<212> TYPE: PRT
<213> ORGANISM: Artificial sequence
<220> FEATURE:
<223> OTHER INFORMATION: synthetic sequence

<400> SEQUENCE: 2

Met Ala Ala Val Thr Leu Asp Glu Ser Gly Gly Leu Gln Thr Pro
1               5                   10                  15

Gly Arg Ala Leu Ser Leu Val Cys Lys Ala Ser Gly Phe Thr Phe Ser
                20                  25                  30

Ser Tyr Asn Met Gly Trp Val Arg Gln Ala Pro Gly Lys Gly Leu Glu
            35                  40                  45

Phe Val Ala Gly Ile Asp Asn Thr Gly Arg Tyr Thr Gly Tyr Gly Ser
50                  55                  60

Ala Val Lys Gly Arg Ala Thr Ile Ser Arg Asp Asn Gly Gln Ser Thr
65                  70                  75                  80

Val Arg Leu Gln Leu Leu Arg Ala Glu Asp Thr Asn Asn Gly Thr Tyr
                85                  90                  95

Tyr Cys Ala Lys Ala Ala Gly Asp Leu Gly Tyr Gly Asp Leu Tyr Ala
            100                 105                 110

Gly Gln Ile Asp Ala Trp Gly His Gly Thr Glu Val Ile Val Ser Ser
            115                 120                 125
```